US010518003B2

(12) United States Patent
Vyas et al.

(10) Patent No.: US 10,518,003 B2
(45) Date of Patent: Dec. 31, 2019

(54) METHOD TO MANUFACTURE THIN STRUT STENT FROM BIOABSORBABLE POLYMER WITH HIGH FATIGUE AND RADIAL STRENGTH

(71) Applicant: MERIL LIFE SCIENCES PVT. LTD., Vapi (IN)

(72) Inventors: Rajnikant Gandalal Vyas, Mumbai (IN); Pramod Kumar Minocha, Vapi (IN); Deveshkumar Mahendralal Kothwala, Surat (IN)

(73) Assignee: MERIL LIFE SCIENCES PVT. LTD., Vapi (IN)

(*) Notice: Subject to any disclaimer, the term of this patent is extended or adjusted under 35 U.S.C. 154(b) by 233 days.

(21) Appl. No.: 15/479,316

(22) Filed: Apr. 5, 2017

(65) Prior Publication Data
US 2017/0203494 A1   Jul. 20, 2017

Related U.S. Application Data

(63) Continuation-in-part of application No. 15/031,804, filed as application No. PCT/IN2014/000729 on Nov. 20, 2014.

(30) Foreign Application Priority Data

Jul. 7, 2014   (IN) .......................... 2208MUM2014

(51) Int. Cl.
*A61L 31/16*   (2006.01)
*A61F 2/915*   (2013.01)
(Continued)

(52) U.S. Cl.
CPC .............. *A61L 31/16* (2013.01); *A61F 2/915* (2013.01); *A61L 31/06* (2013.01); *A61L 31/148* (2013.01);
(Continued)

(58) Field of Classification Search
USPC ......... 29/421.1, 505, 446, 447; 264/85, 129, 264/209.5, 232, 233, 235, 237, 400, 564,
(Continued)

(56) References Cited

U.S. PATENT DOCUMENTS 7,971,333 B2   7/2011   Gale et al.
8,501,079 B2   8/2013   Glauser et al.
(Continued)

FOREIGN PATENT DOCUMENTS

EP   1973502 A1   10/2008
WO   2012145326 A1   10/2012

OTHER PUBLICATIONS

U.S. Appl. No. 15/479,314, Office Action dated Nov. 28, 2018.
(Continued)

*Primary Examiner* — Sarang Afzali
*Assistant Examiner* — Darrell C Ford
(74) *Attorney, Agent, or Firm* — Kunzler Bean & Adamson, PC

(57) ABSTRACT

The invention discloses a process for the preparation of a biodegradable stent which involves deforming an extruded biodegradable polymer tube axially at a first predefined temperature by applying an axial force for a first predefined time interval. The process is followed by radially expanding the axially stretched tube at a second predefined temperature by pressurizing the tube with an inert gas in one or more stages, the pressure applied in each successive stage being higher than the pressure applied in a previous stage. The process further comprises laser cutting a specific pattern of scaffold structure on the expanded tube and then crimping the laser cut stent on the balloon of delivery catheter in a sterile environment in multiple stages.

13 Claims, 11 Drawing Sheets

(51) Int. Cl.

| | | |
|---|---|---|
| *B29C 71/02* | (2006.01) | |
| *B29C 71/00* | (2006.01) | |
| *A61L 31/14* | (2006.01) | |
| *A61L 31/06* | (2006.01) | |
| *A61L 31/18* | (2006.01) | |
| *B29L 31/00* | (2006.01) | |
| *B29K 67/00* | (2006.01) | |
| *B29C 55/26* | (2006.01) | |
| *B29C 55/00* | (2006.01) | |

(52) U.S. Cl.
CPC ............ *A61L 31/18* (2013.01); *B29C 55/005* (2013.01); *B29C 55/26* (2013.01); *B29C 71/0009* (2013.01); *B29C 71/02* (2013.01); *A61F 2002/91575* (2013.01); *A61F 2210/0004* (2013.01); *A61L 2300/416* (2013.01); *B29C 2071/0045* (2013.01); *B29C 2071/022* (2013.01); *B29C 2793/009* (2013.01); *B29C 2793/0045* (2013.01); *B29K 2067/046* (2013.01); *B29K 2995/006* (2013.01); *B29L 2031/7534* (2013.01)

(58) Field of Classification Search
USPC .......................................................... 264/565
See application file for complete search history.

(56) References Cited

U.S. PATENT DOCUMENTS

| | | | |
|---|---|---|---|
| 2007/0043434 A1 | 2/2007 | Meerkin et al. | |
| 2007/0283552 A1* | 12/2007 | Gale ........... | A61F 2/91 29/505 |
| 2008/0051873 A1* | 2/2008 | Cottone ........... | A61F 2/91 623/1.16 |
| 2008/0118546 A1* | 5/2008 | Thatcher ........... | A61L 27/18 424/426 |
| 2008/0206440 A1 | 8/2008 | Cottone | |
| 2009/0146348 A1* | 6/2009 | Huang ........... | A61F 2/91 264/573 |
| 2009/0246253 A1* | 10/2009 | Ding ........... | A61L 31/10 424/426 |
| 2010/0025894 A1* | 2/2010 | Kleiner ........... | B29C 71/0063 264/528 |
| 2010/0042202 A1* | 2/2010 | Ramzipoor ........... | A61F 2/91 623/1.15 |
| 2011/0021717 A1* | 1/2011 | Wang ........... | A61L 31/06 525/411 |
| 2011/0066222 A1 | 3/2011 | Wang | |
| 2011/0118827 A1* | 5/2011 | Wu ........... | A61L 27/46 623/1.46 |
| 2011/0130822 A1* | 6/2011 | Cottone ........... | A61F 2/91 623/1.15 |
| 2011/0190871 A1 | 8/2011 | Trollsas et al. | |
| 2011/0260352 A1* | 10/2011 | Tang ........... | B29C 71/02 264/51 |
| 2011/0260358 A1* | 10/2011 | Wang ........... | A61L 2/087 264/234 |
| 2012/0271396 A1* | 10/2012 | Zheng ........... | A61F 2/82 623/1.2 |
| 2012/0280432 A1* | 11/2012 | Chen ........... | B29C 49/50 264/400 |
| 2013/0187313 A1 | 7/2013 | Glauser et al. | |
| 2013/0238078 A1 | 9/2013 | Sudhir et al. | |
| 2013/0331927 A1* | 12/2013 | Zheng ........... | A61F 2/82 623/1.19 |
| 2014/0074219 A1 | 3/2014 | Hingston et al. | |
| 2014/0263217 A1 | 9/2014 | Pacetti et al. | |
| 2015/0018935 A1 | 1/2015 | Pacetti et al. | |
| 2016/0081827 A1 | 3/2016 | Lumauig et al. | |
| 2016/0243290 A1* | 8/2016 | Vyas ........... | B29C 49/6472 |
| 2017/0203010 A1 | 7/2017 | Vyas et al. | |
| 2017/0203491 A1 | 7/2017 | Vyas et al. | |
| 2017/0203494 A1 | 7/2017 | Vyas et al. | |
| 2017/0266026 A1* | 9/2017 | Kim ........... | A61F 2/958 |

OTHER PUBLICATIONS

Kastrati, et al., "Intracoronary Stenting and Angiographic Results: Strut Thickness Effect on Restenosis Outcome (ISAR-STEREO) Trial", Circulation, Journal of the American Heart Association, 2001: 103: 2816-2821.

Pache, et al., "Intracoronary Stenting and Angiographic Results: Strut Thickness Effect on Restenosis Outcome (ISAR-STEREO2) Trial", Journal of the American College of Cardiology, vol. 41, No. 8 (2003) 8 pages.

PCT International Application No. PCT/IN2014/000729 International Search Report dated Jun. 10, 2015.

PCT International Application No. PCT/IN2014/000729 Written Opinion dated Jun. 10, 2015.

\* cited by examiner

METHOD TO MANUFACTURE THIN STRUT STENT FROM BIOABSORBABLE POLYMER WITH HIGH FATIGUE AND RADIAL STRENGTH

CROSS-REFERENCES TO RELATED APPLICATIONS

This is a continuation-in-part application of and claims priority to U.S. patent application Ser. No. 15/031,804 entitled "THIN STRUT STENT FROM BIOABSORBABLE POLYMER WITH HIGH FATIGUE AND RADIAL STRENGTH AND METHOD TO MANUFACTURE THEREOF" and filed on Apr. 25, 2016 for RAJNIKANT GANDALAL VYAS, et al., which is a nationalization of International Patent Application Number PCT/IN2014/00729 entitled "THIN STRUT STENT FROM BIOABSORBABLE POLYMER WITH HIGH FATIGUE AND RADIAL STRENGTH AND METHOD TO MANUFACTURE THEREOF" and filed on Nov. 20, 2014 for RAJNIKANT GANDALAL VYAS, et al., which claims priority to Indian Patent Application Number IN2014MUM2208 entitled "THIN STRUT STENT FROM BIOABSORBABLE POLYMER WITH HIGH FATIGUE AND RADIAL STRENGTH AND METHOD TO MANUFACTURE THEREOF" and filed on Jul. 7, 2014 for RAJNIKANT GANDALAL VYAS, et al., the entire contents of each of which are incorporated herein by reference for all purposes.

FIELD

This invention relates to the method of manufacture of a balloon expandable stent made from bioabsorbable polymer with thin struts having adequate strut thickness and; high fatigue and radial strength. The invention further relates to a balloon expandable stent made from bioabsorbable polymer with thin struts having adequate strut thickness and; high fatigue and radial strength.

BACKGROUND

Stents are used to treat atherosclerotic stenosis or other type of blockages in body lumen like blood vessels or to expand the lumen that has narrowed due to disease. "Stenosis" is narrowing of the diameter of a bodily passage or orifice due to formation of plaque or lesion. The function of the stent is to expand the lumen diameter by pressing the plaque to the vessel wall and to maintain patency of the lumen of the blood vessel thereafter at the location of its implantation. The stent may be coated with therapeutic agent/s and/or biocompatible material/s for beneficial effects like minimizing the possibility of restenosis, reduction in inflammation etc.

The first step in treatment of stenosis involves locating the region that may require treatment such as a suspected lesion in a vessel by angiography of the diseased vessel followed by implanting a suitable stent. The stent may be balloon expandable type or self-expanding type. The stents are mounted on the delivery catheter which helps in delivering the stent to the target site of the disease.

The balloon expandable stent is mounted on a balloon catheter by crimping process such that it holds tightly over the balloon and attains a considerably lower diameter (profile). The catheter is percutaneously inserted into the body lumen and is directed to the site of the disease (blockage or narrowed lumen). At the site of the disease, the balloon is inflated by application of hydraulic pressure to expand the stent radially to desired diameter. Radial expansion of the stent presses the plaque to the wall of the vessel by which the restriction to the flow of blood in the vessel is removed. The balloon is then deflated by removing the hydraulic pressure and withdrawn from the body of the patient.

On expansion, the stent material attains plastic deformation and hence the stent does not recoil back to its original shape and remains in expanded state keeping the lumen patent. Self-expanding stents are typically made of metal with shape memory and they expand without help of any other device such as balloon. The stent is mounted on the delivery catheter and expansion of the stent is restricted by a sheath. The catheter is percutaneously inserted into the body lumen and guided to the target site where the lesion or plaque is located. The sheath is then retracted to allow the stent to expand. Like balloon expandable stent, this stent also makes the lumen patent by pressing the plaque. The structure of stents is cylindrical with scaffold made up of a pattern or network of interconnecting structural elements i.e. "struts". The scaffolding of the stent may be formed from wires, tubes, or sheets of material rolled into a cylindrical shape. In addition, the surface of the stent may be coated with formulation of therapeutic agent/s and/or biocompatible materials with suitable carriers and additives.

It is important that the stent must be able to withstand structural loads viz. radial compressive forces imposed by the wall of the body lumen on the stent. Radially directed force from the wall of the lumen may tend to cause the stent to recoil inward. The radial strength of the stent must be adequate to resist radial compressive forces. These forces are cyclic in nature due to pulsating blood flow. Hence the stent should have adequate fatigue strength to withstand cyclic loading imposed on it by the lumen. In addition, the stent must possess sufficient flexibility to allow for crimping, maneuvering through the vascular pathway and expansion process. The scaffold structure should also be dense enough to prevent prolapse of the plaque but open enough to allow easy side branch access for another catheter with or without stent. The stent should exhibit required radio opacity for ease of implantation.

Stents have been used effectively for quite a long time and the safety and efficacy of stenting procedure are well established. Implantation of the stent causes some injury to the vessel. The healing process starts and finally the endothelial cells are formed at the implantation site. Once the healing process is completed the endothelial cells provide sufficient support to the wall of the lumen and the stent is no longer required. Thus, the presence of the stent in the lumen is required only for a limited period of time till the healing process is completed.

Coronary stents are generally made from biocompatible materials such as metals which are bio-stable. Metal has high mechanical strength that provides adequate radial and fatigue strength to the stent that prevent early and later recoil. However, the metallic stent remains at the implant site indefinitely. Leaving the stent at the implanted site permanently causes compliance difference in the stented segment and the healthy vessel segment. In addition, there is a possibility of permanent interaction between the stent and the surrounding tissue resulting in a risk of endothelial dysfunction causing delayed healing and late thrombosis.

Drug-eluting stents are a breakthrough in the development of stents with their ability to significantly reduce restenosis rates and the need for repeat revascularization. However, they are still associated with sub-acute and late thrombosis that necessitates prolonged antiplatelet therapy for at least 12 months.

Metallic stents have been used effectively for quite a long time and their safety and efficacy are well established. The main issues of a stent are restenosis and in-stent thrombosis. One of the important causes of these adverse effects is injury of the artery caused by implantation of the stent. The injury leads to restenosis and delayed endothelialization. These adverse effects can be reduced if injury to the artery is reduced. It is well established that the thickness of the struts of a stent plays an important role in injuring of the artery. Thinner struts cause less injury compared to thicker struts. Thus, the injury of the artery can be reduced by making the struts as thin as practically possible.

While deciding the thickness of the struts, care should be taken so that important mechanical properties of the stent like radial strength and fatigue resistance are adequate to withstand forces imposed by the body lumen like artery.

The injury to the artery wall can thus be minimized by reducing the thickness of the struts of the stent scaffold structure. It is well established that the stent with less strut thickness causes less injury compared to the stent with thicker struts. This subject is discussed in detail by Kastrati A, Schömig A, Dirschinger J, et al. in their paper "Strut Thickness Effect on Restenosis Outcome (ISAR STEREO Trial)" published in Circulation 2001; 103:2816-2821. The incidence of angiographic restenosis was 15.0% in the group of patients treated with stents of thin struts against restenosis of 25.8% in the group treated with stents with thicker struts. Clinical restenosis was also significantly reduced, with a reintervention rate of 8.6% among thin-strut patients and 13.8% among thick-strut patients.

These findings were reconfirmed by Kastrati A, et al in their paper "Strut Thickness Effect on Restenosis Outcome (ISAR STEREO-2 Trial)" published in J. Am. Coll. Cardiol, 2003; 41:1283-8. The incidence of angiographic restenosis was 17.9% in the group of patients treated with stents of thin struts against restenosis of 31.4% in the group treated with stents with thicker struts. Target Vessel Revascularization (TVR) due to restenosis was required in 12.3% of the patients in thin strut group against 21.9% required in patients of the thick strut group.

In conclusion from above it was established that the use of thinner strut device is associated with a significant reduction in angiographic and clinical restenosis after coronary stenting. The stents can be made from polymeric materials which are bio-absorbable/biodegradable.

A biodegradable stent can be configured to degrade and disappear from the implant site when it is no longer needed leaving behind only the healed natural vessel. This will allow restoration of vasoreactivity with the potential of vessel remodeling. These stents are believed to improve the healing process whereby the chances of late stent thrombosis are reduced considerably. Prolonged antiplatelet therapy then may not be necessary. The biodegradable stents may be made from biocompatible polymers such as Poly-L-lactic acid (PLLA), polyglycolic acid (PGA), poly (D, L-lactide/glycolide) copolymer (PDLA), and polycaprolactone (PCL). Poly-L-lactic acid (PLLA) is usually recommended polymer among others.

The only disadvantage of polymeric materials is their lower mechanical strength compared to the metals. Strength to weight ratio of a polymeric material is smaller than that of a metal. This makes it necessary to increase thickness of the polymeric stents compared to metallic stents to get adequate radial and fatigue strengths. The increase in thickness results into higher profile and higher degree of injury to the blood vessel. Higher thickness reduces the flexibility of the stent resulting into poor trackability through tortuous arteries. Polymeric materials have poor radio opacity. Polymeric materials are also brittle under conditions within human body.

It is hence necessary to select right polymer and modify its mechanical properties to make it suitable for stent application. Making the stent with low strut thickness poses additional challenge. Selection of a polymeric material, design of stent scaffold structure and process for making a stent require careful attention to several aspects. The stent should have adequate mechanical strength to prevent recoil. The rate of degradation of the polymer should be such that the mechanical strength of the stent is retained to provide support to the vessel and prevent prolapse of the plaque into the vessel till the healing process is complete. The stent should eventually disappear by degradation. The stent should have enough flexibility for ease of crimping on the balloon of the catheter and for good trackability through the tortuous passages through arteries. The polymeric material and its degradation products should be biocompatible. The rate of degradation will influence the release profile of the therapeutic agents coated on the stent. Polymers such as Poly-L-lactic acid (PLLA), polyglycolic acid (PGA), poly (D, L-lactide/glycolide) copolymer (PDLA), and polycaprolactone (PCL) and their degradation products are known to be non-toxic and biocompatible.

There is a continuing need for manufacturing and fabricating methods for polymeric stents with such scaffold design that offer adequate radial strength, fracture toughness, low recoil and sufficient shape stability with low strut thickness. A stent with low strut thickness will result in low injury to the arterial wall. In addition, thin stent will give lower profile in crimped condition compared to a stent with higher strut thickness. Stents with thinner struts impart more flexibility to the stent. There is ample literature available on biodegradable stents and the process for manufacturing the same.

U.S. Pat. No. 7,971,333 describes a method of forming a stent from polymeric materials by modifying the mechanical properties of polymer tube to get desirable mechanical properties. The polymer can be modified to increase the strength, modulus and/or toughness of the polymer tube to make them comparable to metal. Mechanical properties of a polymer can be modified by applying stress to the polymer preferably above its glass transition temperature ($T_g$) followed by heat setting. This induces molecular orientation of polymer chains in radial and axial directions. The stress is applied to the polymer tube by expanding it radially by blow molding and by stretching the tube axially by applying axial load that result into biaxial orientation of polymer molecules. The tube is heated to desired temperature by heating the mold. Radial deformation of the tube is achieved by pressurizing the tube in the mold with inert gas under pressure. The degree of radial deformation is defined as ratio of outside diameter of tube after expansion and original internal diameter of tube. This ratio may vary between 1 and 20 or narrowly between 2 and 6. Degree of axial deformation is defined as ratio of lengths of tube after and before deformation. Temperature and degree of deformation affect crystallinity which in turn is dependent on crystallinity of the tube before deformation. The patent describes laser cutting of the deformed tube to get the scaffold structure of the stent.

U.S. Pat. No. 8,501,079 discloses method for fabricating a stent from PLLA tube; radially and axially expanding the tube inside a mold while the tube is heated to a processing temperature; wherein the processing temperature is 84° C. The radial and axial expansion percentages are 400% and 20% respectively to produce an expanded tube having an increased mechanical strength, fracture toughness and homogeneity in mechanical properties over the wall thickness of the expanded tube; and forming the stent from the expanded tube. The radial expansion of the tube is achieved at a pressure of 110-140 psi.

US 2013/0187313 discloses a method for fabricating stent comprising providing a PLLA tube disposed within a cylindrical mold; heating the mold and the tube to a tube deformation temperature (80° C. to 115° C.) with a heat source translating along the cylindrical axis of the mold and the tube, wherein the heat source translation rate is between 0.2-1.2 mm/sec; increasing the pressure inside the tube; allowing the increased pressure in the tube (110-140 psi) to radially expand the tube against the inner surface of the mold, wherein the radial expansion propagates along the cylindrical axis of the mold and tube as the heat source translates along the cylindrical axis, applying a tensile force to the tube along the cylindrical axis during the radial expansion to axially elongate the tube during the radial expansion, wherein the percent radial expansion is 300-500% and the percent axial elongation is 100-200%; and forming a stent pattern in the axially expanded and radially deformed tube.

EP1973502 reports a stent comprising a deformed spherical radio opaque marker disposed in a depot in a portion of the stent, the marker being coupled to the portion at least partially by an interference fit between an expanded portion of the marker and an internal surface of the portion of the stent within the depot, wherein the marker comprises sufficient radio opacity for ease of imaging by normal imaging techniques. Gaps between the deformed marker and the internal surface are filled with a polymeric coating material.

US 2011/0066222 describes method of forming a stent from PLLA tubular polymer that is deformed in a blow mold. Desired polymer morphology resulting in improved stent performance is obtained with axial expansion ratio from about 10%-200%, preferably 20% to 70%, a radial expansion ratio from about 100%-600%, preferably 400% to 500%, axial deformation propagation at or about 0.3 mm/min, selected expansion pressure of about 50 to 200 psi, preferably 130 psi and expansion temperature about 100° F. to 300° F. preferably less than 200° F. Heating is done by a moving heat source outside the mold. The heat source is moved at the rate of 0.1-0.7 mm per minute. The stent may be made of PLGA, PLLA-co-PDLA, PLLD/PDLA stereo complex, and PLLA based polyester block co-polymer containing a rigid segment of PLLA or PLGA and a soft segment of PLC or PTMC.

None of the prior art mentions the design and manufacturing method for making polymer stent with low strut thickness (less than 130 μm, preferably 100-110 μm thickness). The polymer stents have potential shortcomings compared to metal stents of the same dimensions viz. lower radial strength and lower rigidity of the polymer stents compared to metallic stents. Lower radial strength potentially contributes to relatively high recoil of polymer stents after implantation into an anatomical lumen. Another potential problem with polymer stents is that struts can crack or fracture during crimping, delivery and deployment, especially for brittle polymers. Due to these shortcomings, the strut thickness of the polymer stents is always kept higher compared to the metallic stents with same radial and fatigue strength.

In conclusion from "ISAR STEREO Trial" and "ISAR STEREO-2 Trial" as described above, it was established that the use of thinner strut device is associated with a significant reduction in angiographic and clinical restenosis after coronary stenting.

Thus, there is a continuing need for identifying right polymer and manufacturing and fabricating methods for polymeric stents of right scaffold design that impart sufficient radial strength, fracture toughness, low recoil and sufficient shape stability at low strut thickness. Additional advantage of a stent with low strut thickness is its lower profile after it is crimped on the balloon of the delivery catheter and more flexibility. Making a stent with desired low strut thickness starts with choosing a right polymeric material. The polymeric material then undergoes a number of process steps like drawing the tube from this material, modifying the mechanical properties of the tube, making the stent from this tube with right scaffold design, crimping the stent on the balloon of the delivery catheter and sterilization of the assembly.

The tube of the chosen polymer may be formed by extrusion or molding process under controlled conditions to achieve desired properties of the tube. Processing conditions that affect tube properties mainly include draw down ratio during extrusion, temperature at which the tube is extruded (relative to glass transition temperature and melting point of the polymer) and tube diameter.

Mechanical properties of a polymer can be modified by applying a stress. The stress alters the molecular structure and/or morphology of the polymer. The degree and rate of changes in mechanical properties depend on the temperature at which the stress is applied and degree of deformation the polymer (the tube in this case) undergoes due to application of the stress. The stress can be applied to the polymer tube in radial and axial directions to modify the crystalline morphology and polymer chain orientation in controlled manner to achieve a desired combination of strength and fracture toughness along axial and radial directions. Combined with right scaffold design, the strut thickness can be reduced while maintaining high fatigue and radial strength and keeping recoil under control. At the same time, it is necessary to achieve desired degradation rate of the polymer such that the stent retains adequate mechanical strength till the healing process of the lumen is completed and the stent eventually disappears from the implant site. The processing of the tube in this way changes the crystallinity of the polymer which in turn influences the degradation rate of the polymer. Amorphous polymer degrades faster than crystalline polymer but it is mechanically weaker than the crystalline polymer. Hence, a balance is required to be achieved in processing of the tube such that the stent has right combination of mechanical strength and degradation rate.

In the light of the above there is a need in the art to develop a biodegradable polymer stent with thin struts from a bioabsorbable polymer with adequate fatigue and radial strengths and a method to manufacture thereof. The process begins with choosing right grade of polymer and setting extrusion process to get desired properties of extruded tube. The grade of the polymer is characterized broadly by its molecular weight, glass transition temperature ($T_g$), crystallinity ($X_c$), molecular structure, and stereo isomerism. Further processing of the tube into stent and the scaffold design of the stent structure should be such as to achieve desired mechanical properties of the finished stent. The processing of the tube includes application of stress to the tube, laser cutting, cleaning of the cut stent, radio opaque marker deposition, heat treatment, drug coating, crimping and sterilization.

The mechanical properties are largely dependent on polymer characteristics like average molecular weight and molecular weight distribution. These characteristics undergo change at each processing stage. Hence it is necessary to check these characteristics at each process stage and devise a process that results in high mechanical strength of the finished stent.

Sterilization of the stent is done by e-beam radiation and this step requires special attention. The e-beam radiation causes degradation of polymer and thus has a significant effect on the average molecular weight of the bioabsorbable polymer and hence its mechanical properties. The current inventors have studied the effect of e-beam radiation on polymer over a wide range of e-beam doses and found that reduction in the e-beam dose improves the mechanical strength of the polymer. Normal dose of e-beam for effective sterilization is more than 20 kGy. The dose can be reduced to some extent by adding stabilizer/s in the polymer matrix. This stabilizer should be biocompatible and should not create any adverse clinical effect.

Therefore, one of the objectives of the instant invention is to get effective sterilization with e-beam dose considerably lower than 20 kGy without use of any additive.

Accordingly, the objective of the invention is to provide a biodegradable/bioabsorbable stent made from a bioabsorbable polymer with thin struts (thickness 130 μm and less, preferably with thickness of 100-110 μm) which has adequate fatigue strength, radial strengths and low recoil and a method for manufacture thereof, for which protection is sought.

SUMMARY

The terms "bioabsorbable" and "biodegradable" are used interchangeably throughout the specification and the same may be appreciated as such by the person skilled in the art. In accordance with the above objectives, the present invention discloses a process for preparation of biodegradable polymer stent preferably made of PLLA (poly-L-Lactide).

In accordance with the above objectives, the present invention discloses a process for preparation of biodegradable polymer stent made of PLLA (poly-L-Lactide) with strut thickness of less than 130 μm which comprises providing an extruded biodegradable polymer tube; deforming the extruded biodegradable polymer tube axially at a first predefined temperature by applying an axial force for a first predefined time interval; radially expanding the axially stretched tube at a second predefined temperature by pressurizing the tube with an inert gas in one or more stages, the pressure applied in each successive stage being higher than the pressure applied in a previous stage; cutting specific pattern of scaffold structure on the expanded tube by laser machining; and crimping the laser cut stent on the balloon of delivery catheter in clean environment in multiple stages.

Accordingly, the invention further encompasses balloon expandable stent made from bioabsorbable polymer with thin struts (e.g. strut thickness 130 μm or less, preferably 100-110 μm) with high fatigue and radial strength.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
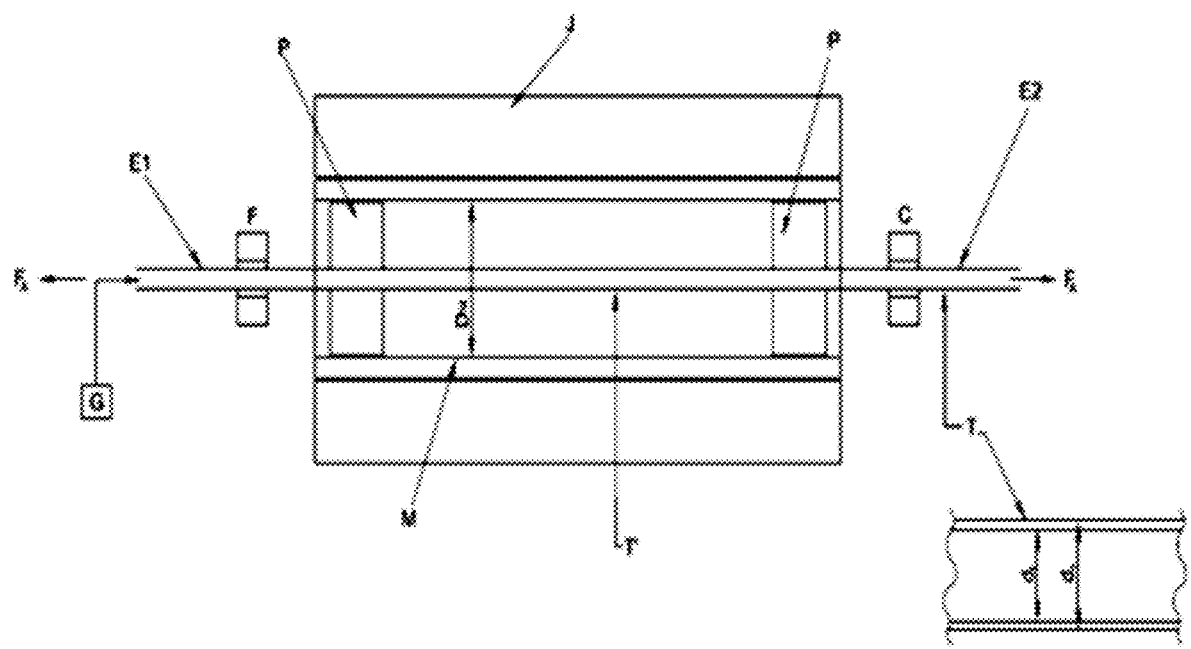
FIG. 1 is a view depicting the mold system where the polymer tube is processed.

The present invention discloses a biodegradable stent with thin struts having adequate fatigue and radial strength as well as low recoil and its method of manufacture thereof. The tube may be made from right grade of PLLA polymer and a method of manufacture thereof. The various embodiments of the present invention describe the polymer properties and manufacturing of the stent. Present invention can be applied to balloon expandable stents, stent grafts or stents for other vascular applications.

The mechanical properties of a polymer depend largely on characteristics like average molecular weight and molecular weight distribution. The polymer has different size and types of monomer chains. Molecular weight of a polymer can be described by weight average molecular weight $M_w$ and number average molecular weight $M_n$. $M_w$ represents average molecular mass of various molecular chains of the polymer which includes even those having same types of individual macro molecules of different chain lengths. $M_n$ represents the average of different sizes of various polymer chains and it is arithmetic mean or average of the molecular masses of the individual macromolecules. The $M_w$ and $M_n$ can be determined by gel permeable chromatography (GPC). Another important parameter for a polymer is the poly dispersity index (PDI) which is the ratio of $M_w$ to $M_n$ ($M_w/M_n$). This parameter gives an indication of how narrow the molecular distribution is.

A parameter closely related to $M_w$ and $M_n$ is the intrinsic viscosity which can be measured using Brookfield viscometer (e.g. Brookfield viscometer model LVDV E230). In addition, other parameters described further are important for the polymer. Glass transition temperature $T_g$, and melting temperature Tm are important thermal properties. Processing of a polymer at elevated temperatures results in the change in morphology of a polymer and influences its crystallinity $X_c$. $X_c$ defines the degree of crystallinity of a polymer in percentile value. A totally amorphous polymer has $X_c$ value of 0% and a fully crystalline polymer has $X_c$ value of 100%. Polymers with higher microcrystalline regions (higher $X_c$) are generally tougher and more impact-resistant than polymers with lower microcrystalline regions (lower $X_c$).

Since PLLA is the polymeric form of an optically active monomer, specific rotation of PLLA is also an important characteristic. Polymers obtained from optically active monomers are semi crystalline while optically inactive monomers give amorphous polymers. Crystalline polymer has higher mechanical and thermo mechanical properties as described above. The difference in mechanical properties are related to the stereo regularity of the polymer chains which are characterized by presence of only S (−) chiral centers. For example, the propensity for the lactide monomer to undergo racemization to form meso-lactide can impact optical purity and thus material properties of the polymer at higher temperatures.

All these characteristics influence the mechanical properties of the polymer used for the process of making the stent.

In the present invention, for making a bioabsorbable stent, a number of bioabsorbable polymers like PLLA, PLGA, PDLA etc. of various molecular weights were studied. It was observed during the study that $M_w$ and $M_n$ and also other characteristics change at each step of the stent manufacture i.e. starting with extrusion of the tube till sterilization. Observation of these properties under various processing conditions gave valuable insights which helped in making the finished stent with adequate mechanical strength in spite of low strut thickness. Specific scaffold design also played an important role in achieving low strut thickness.

The polymer tube can be formed using extrusion or molding process. During extrusion or molding process, a polymer e.g. PLLA can undergo thermal degradation, leading to formation of lactide monomers and other by-products which result in reduction of molecular weight of the polymer. Dependence of mechanical properties of PLLA with its molecular weight is well investigated; the strength increases with increase in molecular weight. Degradation of the polymer causes reduction in its average molecular weight. Hence, excessively high temperatures should be avoided during extrusion to avoid degradation of the polymer.

The extrusion of a tube is done at about melting point of the polymer and significant decrease in average molecular weight $M_w$ as well as $M_n$ was observed in all the types of bioabsorbable polymers. It was observed that under similar conditions, % reduction in $M_w$ was dependent on the $M_w$ before extrusion process. This means that % reduction in $M_w$ was higher for polymer with higher $M_w$ compared to the polymer with lower $M_w$. For example, $M_w$ of PLLA before and after extrusion were found to be 765230 and 590780 respectively which amounted to 22.8% reduction in $M_w$. Another PLLA with $M_w$ 622480 under similar conditions showed $M_w$ 496490 after extrusion i.e. $M_w$ reduced by 20.24%. Similar results have also been observed in case of PLGA and PDLA tubes.

In both the above cases, the % reduction in average molecular mass $M_n$ was higher than $M_w$. In the former case, $M_n$ reduced from 563340 to 355280 i.e. 36.94% and in latter case, $M_n$ reduced from 459630 to 307720 i.e. 33.05%. Thus, the extrusion conditions can influence the properties of the polymer in a significant manner. It is also important to note that mechanical properties of the extruded tube are also dependent on the stresses applied during extrusion process and the other process parameters.

Mechanical properties of polymer depend on molecular orientation of the polymer chains. Molecular orientation of polymer chains is altered when stress is applied to the polymer. The reorientation of the molecular chains occurs in the direction of the applied stress. The extent to which the orientation of polymer chains gets altered depends on the temperature at which the stress is applied and the magnitude of the stress. Generally, for altering the molecular orientation, this temperature should be above glass transition temperature ($T_g$) of the polymer and lower than its melting point. The stress can be applied in axial and radial directions to orient the polymer molecules axially and circumferentially.

The application of the stress also influences crystallinity of the polymer. As mentioned above, mechanical properties of the polymer also depend on its crystallinity. Crystallinity increases the mechanical strength of the polymer. Crystallinity also influences the degradation rate of the polymer. Increase in crystallinity decreases the degradation rate.

The method of manufacture and scaffold structures described below are with respect to PLLA as polymer. However, the aspects of this invention can be applied to other polymers and one skilled in the art can adopt the aspects of this invention by optimizing them for different biodegradable and biocompatible polymeric materials.

Figure 2:
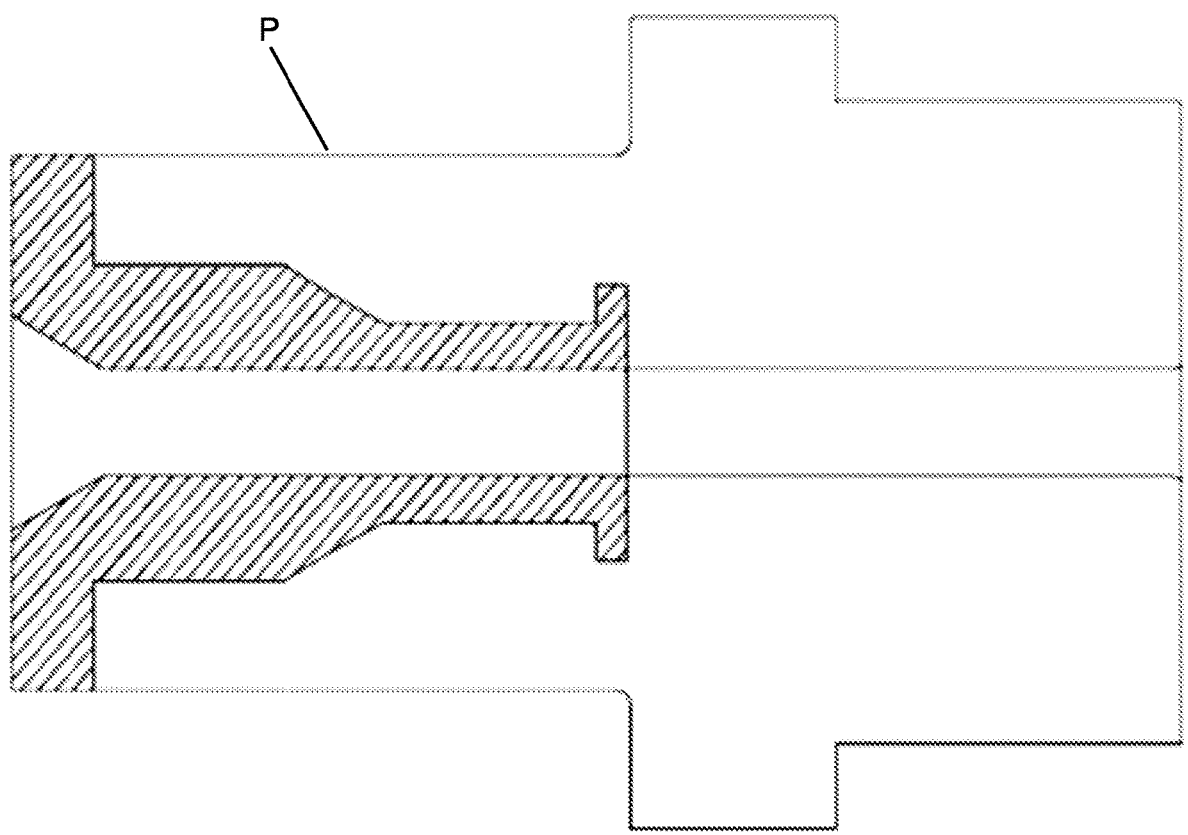
FIG. 2 depicts details of the end plug to hold the tube.
Figure 3:
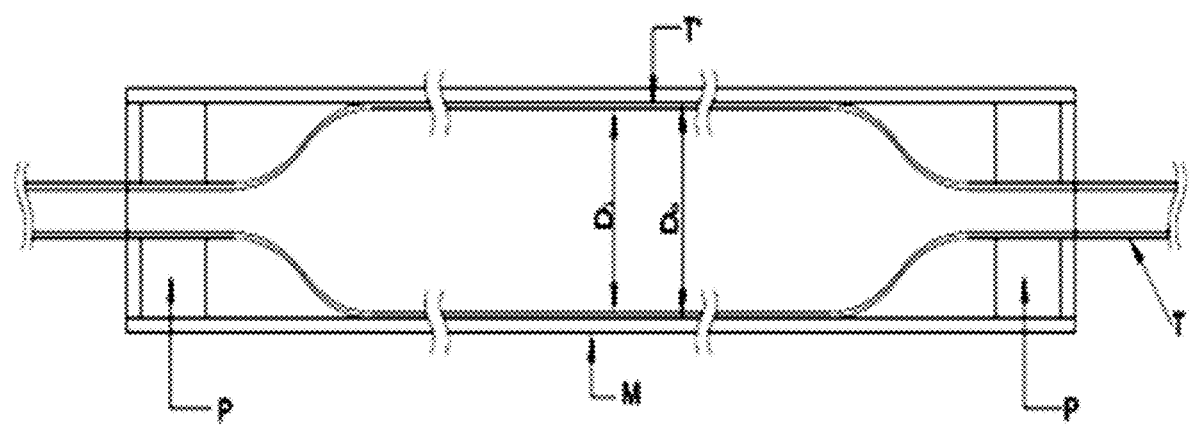
FIG. 3 depicts polymer tube inside the mold under process of radial deformation.

Accordingly, in a preferred embodiment, the invention provides a detailed method for manufacturing a polymer (PLLA) stent as described below:

a. The polymer tube is made by extrusion or injection molding. The process conditions and equipment should produce the tube with desired internal diameter $d_i$ and external diameter $d_o$. In the instant invention, the polymer tube was made by extrusion process and $M_w$ of the polymer tube ranged from around 590000 to 620000, $M_n$ ranged from around 350000 to 370000, and crystallinity ranged from approximately 7% to 12%.

b. The extruded polymer tube T with internal diameter $d_i$ and external diameter $d_o$ is placed centrally in the mold M (depicted in FIG. 1). Mold M can be cylindrical in shape and can be made from metal with good thermal conductivity. The mold M has inside diameter DM as shown in FIG. 1. The polymer tube T can be aligned centrally in the mold by use of end plugs P provided at both ends of the mold M. Details of the end plug P are depicted in FIG. 2. The portion of the polymer tube T inside the mold M is designated as T'.

c. Two ends (proximal end E1 and distal end E2 as depicted in FIG. 1) of the polymer tube T are held firmly outside the mold in fixtures F and C. The distal end of the tube T can be fixed to fixture C such that this end of the tube T gets crimped and sealed. Both the fixtures (F and C) can be moved by applying axial force FA equally on both fixtures which gets transmitted axially to the tube T.

d. The proximal end E1 of the tube T can be connected to a source of inert gas G (as depicted in FIG. 1) which can supply the inert gas under pressure inside the tube T.

e. The mold M can be covered by jacket J (shown in FIG. 1) which has heating and cooling arrangement. The heating can be done electrically and cooling by suitable cooling medium. The jacket J does the heating and cooling of the mold M which in turn heats and cools the polymer tube T. The heating and cooling system is capable of heating or cooling the mold M and the tube T' uniformly. High thermal conductivity of the mold helps in uniform heat transfer for the jacket J, the mold M and the tube T' inside the mold. Temperature indicators are provided at critical locations to exhibit the temperature in the mold M.

f. The electrical heating can be turned on in the jacket J and the tube T' can be heated to temperature approximately between 60° C. and 80° C., preferably between around 74° C. and 76° C.

g. The tube T can then be axially deformed (elongated) by applying tensile force FA to both the fixtures (F and C). The temperature of the portion of the tube which is inside the mold M (T') can be higher than rest of the tube (T). Hence, this portion will start deforming axially i.e. its length will increase. The axial force can be applied till desired elongation of tube T' can be achieved. The ratio of final length of the tube to its initial length is termed as "axial expansion ratio". This ratio can be kept between 1.05 and 1.7.

h. The conditions in the mold (tensile force and the temperature) at this stage can be held for 15-20 sec to set the tube condition. Then the tensile force can be removed.

i. Inert gas like nitrogen under pressure from the inert gas source G can be then introduced in the tube through its proximal end E1 while maintaining the temperature. As the distal end E2 of the tube T can be crimped and sealed at C, the pressure in the tube T/T' will increase. The temperature of the portion of the tube which is inside the mold M (T') can be higher than rest of the tube (T). Hence, this portion will start deforming radially i.e. its diameter will increase. The inert gas pressure can be applied in two or more stages, preferably in three stages. The stage wise application of inert gas pressure improves the mechanical properties further, reduces recoil considerably and eliminates possibility of formation of cracks and waviness on the surface of deformed tube T'. The external diameter of the deformed tube T' will increase till the external surface of the tube contacts internal surface of the mold M as depicted in FIG. 3. The inside diameter (DM) of the mold M restricts the extent of deformation of tube T'. The internal and external diameters of the tube T' will increase to $D_i$ and $D_o$ respectively as shown in FIG. 3. The ratio of internal diameter of expanded tube $D_i$ to original tube diameter $d_i$ is termed "radial deformation ratio". $D_o$ is dependent on the internal diameter of the mold $D_M$. Hence, the internal diameter of mold M ($D_M$) is kept such that the desired radial deformation ratio is achieved. The radial deformation ratio is kept approximately between 3 and 5.

The inert gas pressure and the temperature in the mold M are maintained for few seconds e.g. 15-20 sec after each stage to set the condition. While maintaining the inert gas pressure in the tube, the temperature of the tube is raised, for example, to 100-125° C. and maintained for a specific period of time, preferably 2 minutes to achieve consistent properties of the tube.

Cooling medium is then introduced in jacket J to cool the mold M and the deformed tube T' which is then removed from the mold M.

j. The deformed tube can be then cut on the laser machine to form the stent scaffold structure on the tube.

k. Radio opaque markers can be then fixed on the stent.

l. The laser cut stent with radio opaque markers can then be annealed under vacuum to get consistent polymer morphology throughout the scaffold. This step helps to remove residual monomers and reduced lot to lot variation of the properties. The aim of this step is not to increase crystallinity. There is very little change in crystallinity of the polymer during this step.

m. The stent is then cleaned with suitable solvent to remove any surface irregularities and achieve smooth surface, followed by removal of solvent under vacuum.

n. The stent is then coated with the formulation of therapeutic agent like antiproliferative drug.

o. The stent is then crimped on the delivery device viz. catheter (e.g. between 25° C. and 40° C.).

p. The crimped stent along with the delivery system is then sterilized (e.g. using e-beam). Each manufacturing step described above affects polymer properties like molecular weight, crystallinity, molecular orientation etc. This in turn changes the mechanical properties of the polymer. The mechanical properties of the finished stent should be adequate to demonstrate sufficient radial and fatigue strengths as well as low recoil. The stent should have desired degradation rate so that the stent provides adequate support to the blood vessel till it is healed and eventually disappear from the implant site.

Due to axial and radial deformations, the length and the diameter of the tube undergo change. Hence, the thickness of the tube will change. Thickness of the deformed tube T' will be lower than that of the original tube T. To get the stent of desired thickness, the thickness of the deformed tube should be controlled by choosing the original tube T with specific internal and outer diameters $d_i$ and $d_o$ and deformation ratios to get desired dimensions of the processed (deformed) tube ($D_i$ and $D_o$). These dimensions determine the strut thickness of the finished stent scaffold. The tubular mold used for deforming the tube can be made of metal like high grade of beryllium copper which has very good thermal conductivity.

A simple end plug P can be used at both ends of the mold to keep the tube at the center of the mold. Details of plug P are depicted in FIG. 2. This leads to uniform heating of the tube which ensures uniform axial and radial expansion of the tube in the mold. This in-turn results in uniform thickness of the deformed tube. For this process, use of complicated arrangement like heat source which translates across the mold surface at controlled rate is not required.

In a specific embodiment, inert gas pressure is applied to the tube in three stages i.e. approximately 250-520 psi in stage 1, followed by approximately 375-600 psi in stage 2 and finally approximately 500-670 psi in stage 3. Temperature is maintained approximately between 60° C. and 80° C., preferably between 74° C. and 76° C. Stage wise application of such relatively higher pressures ensures deformation of the tube T' with tight tolerance and elimination of cracks and wavy surface. After each stage, the conditions (pressure and temperature) are maintained for a period of time (e.g. varying between 15 and 20 seconds) to set the tube under each of these conditions. While maintaining the pressure of the last stage i.e. 500-670 psi, the tube is heated to a temperature approximately between 90° C. and 125° C., preferably between 100° C. and 125° C. and maintained for few seconds (e.g. 30 sec to 2 minutes). The tube is then cooled to about 20° C. for few seconds (e.g. 20-30 sec). The pressure is then released and the tube is then removed from the mold. The tube at this stage achieves consistent properties. The crystallinity at this stage is less than 45%.

The three stage pressurization of the tube offers advantage over a single stage. The overall % reduction in $M_w$ and $M_n$ after annealing was lower in case of three stage pressurization compared to single stage pressurization. The Poly dispersity index PDI was lower in case of three stage process compared to single stage which indicated narrow molecular weight distribution. The three stage pressurization resulted in the deformed tube with tight tolerance and free of cracks and wavy surface.

In yet another embodiment, laser cutting of the deformed tube is done using femto seconds equipment and laser beam of about 1300 to 1600 nm wavelength to cut polymer scaffold on the processed tube. The laser cutting process creates the stent scaffold pattern which may consist of struts which are structural elements formed on the tube by laser cutting process. The diameter of the tube after radial expansion may be between initial diameter of the tube ($d_i/d_o$) and expanded diameter of the finished stent. The scaffold structure of a stent has repetitive radially expandable rows of geometrical shapes across its circumference which may be termed as cylindrical elements forming rings. The shape of an element and the way such elements are interconnected with each other can be manipulated to achieve different structural properties i.e. mechanical strength which imparts resistance to radial forces applied to the stent structure by the vascular lumen walls. There exists large design flexibility in creating different shapes. This flexibility should be used keeping in mind other desirable properties of the stent. The stent structure is formed by placement of these elements in a specific pattern to form specific shapes and interconnected array of struts. The elements in the pattern should be close enough such that on expansion of the stent, the plaque or dissections of the body lumen are effectively pressed back in position against the wall of the lumen giving adequate support to prevent tissue prolapse. At the same time, these elements should not be as close as to affect flexibility adversely, interfere with each other during crimping of the stent on the balloon of a catheter or exhibit inadequate access to the side branch in the vascular lumen. The design should be stiff enough to impart required radial and fatigue resistance strengths to the stent. The elements should undergo enough plastic deformation on expansion at specified pressure such that the elastic recoil is within acceptable limits. When the stent is expanded radially, its diameter increases which causes change in its length. The shape and arrangement of the elements should compensate this change in stent length to maintain the original length as far as possible keeping it within acceptable limits. This is achieved by causing the specific strut elements to elongate in unison with radial expansion. Though different sections of the stent may have different mechanical strength across its axis, the stent should achieve its specified diameter uniformly across its entire length when the rated deployment pressure is applied to the balloon catheter. The design should offer adequate grip of the crimped stent on the balloon of the catheter to resist dislodgement during delivery and minimum recoil after expansion of the stent at diseased site of the body lumen. The scaffold structure should allow re-intervention when the stent is implanted in a lumen which has a side branch i.e. it should offer adequate side branch access. In such a case, the structural cells should create sufficiently large opening without breaking the struts when another catheter with or without a stent is inserted through the struts of implanted stent. The structure should have adequate strength and flexibility to withstand all forces of crimping on the balloon of the catheter, maneuvering through the vascular lumens, expansion/deployment at the diseased site and cyclic forces induced by the vascular lumen.

In one embodiment, the stent may have rows of cylindrical elements or struts which form rings. These cylindrical elements are interconnected by cross linking elements or struts. The shape formed within the two consecutive cylindrical elements and two consecutive cross linking elements forms a 'cell' or 'cell structure'. The way such elements are interconnected with each other can be manipulated to achieve different structural properties. Design flexibility is achieved by making these cells with varying lengths and widths. Cells with larger length and width will give lower strength. On the other hand, cells with shorter length and width will give higher strength. For same strut thickness, the struts with higher width will have higher strength and offer more resistance to compressive forces of the arterial wall compared to struts of less width. The terms 'element' and 'strut' are used interchangeably throughout this specification.

The scaffold structure of the stent of present invention generally consists of multiple rows of sinusoidal wave type cylindrical elements with regular or irregular shapes with plurality of peaks and valleys across its axial length of the stent. The cells are formed by connecting upper and lower rows of cylindrical elements with straight or curved links ("cross linking elements" or "cross linking struts"). These cross linking elements connect upper and lower rows of cylindrical elements anywhere along the length of the sides of the elements. These interconnections form cylindrical scaffold structure of the stent.

The cross linking struts provide flexibility to the stent for easy maneuvering of the stent in curved and tortuous paths of the body lumen. The structural strength of the irregular curvilinear cylindrical element can be changed by changing the location where the crosslinking struts are attached along the length of the element. In the embodiments described in this invention, these linkages are located at peaks and valleys or nearly at the center of respective sides of the elements. The width and shape of individual strut and the cell are designed such as to provide effective crimping, to impart sufficient radial strength in expanded state and at the same time to keep recoil and change in length within acceptable limits. The scaffold structure after expansion gives acceptable side branch access. The irregular curvilinear line structure has varying degrees of curvature in regions of the peaks and valleys. The curvature can be varied to impart different structural strength. The shape should give uniform and low crimped profile as well as uniform radial expansion of individual elements around the circumference of the stent in a section and in individual layers along the axis of the stent. When rated deployment pressure is applied to the stent through the balloon of the catheter, the stent attains a uniform diameter across its entire length in spite of having differential strength of elements axially.

The sinusoidal scaffold structures are designed with struts and straight or curved connecting linkages to give segments which are highly flexible. On expansion of the stent during its deployment, these segments deform circumferentially from crimped diameter to an enlarged expanded diameter. Different radial expansion characteristics can be obtained by changing size, shape and cross-section of the sinusoidal element and cross linking struts. In addition, the radial strength of the stent can be increased by increasing the number of cells in a row. Similarly, the strength of the cells can be increased by increasing the number and width of the cross linking struts. The location where the crosslinking struts connect the upper and lower rows of cells can also be manipulated to increase the strength and the overall flexibility of the stent.

The shape of the cells can be changed by changing the curvature of their sides. In a limit, they can be given shape of a straight line. Such changes can make a difference in overall strength of the cell and hence the strength of the row and stent structure as a whole.

The geometry of the interconnected scaffold structure of the stent is so designed that the elastic recoil and change in length of the stent on expansion are kept within acceptable limits.

The number of rows of elements to from cells is dictated by overall length of the stent. The number of cells in a row along the circumference of the stent, defined as crowns, is dictated by the diameter of the stent and width of the cell. The number of crowns can be changed keeping balance with crimping profile.

The overall configuration of the stent decides the radial strength, flexibility and fatigue resistance of the stent. The dimensions of each cell and their spacing are adjusted close enough to prevent protrusion of the plaque or any part of the body lumen where the stent is implanted. At the same time, these dimensions are adjusted to achieve trouble free crimping of the stent over the balloon of the catheter without compromising the flexibility of the stent. The spacing is also adjusted to give desired side branch access. This configuration gives uniform coverage of lumen wall with the stent struts after the stent is fully expanded. The stent gets nicely and firmly opposed in the body lumen. During deployment, the individual elements of sections may be disturbed slightly relative to adjacent cylindrical elements without deforming the overall scaffold structure. After the stent is expanded, portions of the elements may slightly tip outwardly and embed in the vessel wall a little to position the stent properly in the body lumen. This aids in opposing the stent firmly in place after expansion.

The configuration of the individual cells, the cross linking elements and their interconnections are designed to distribute the stresses during crimping and expansion uniformly across the entire stent.

The interconnection of cells with each other is achieved by the cross linking elements as described above. These linkages are connected either at peak or the valley of the element forming the sinusoidal wave type shape of a cell. These linkages can also be connected nearly at the center of the side of the element forming the sinusoidal wave type shape of a cell. This gives a structure which is in the form of a well-supported structural beam in which the unsupported length is reduced at the connection point of cross linking element like a cross linked truss girder beam. The cross linking elements can also be connected off-center to the side elements of the cells. This will divide the unsupported length of this element in 3 sections. The unsupported length of these elements depends on the positions of these cross linking elements. The elements of the cells undergo full plastic deformation after expansion to keep elastic recoil well within acceptable limits.

The configuration of the stent scaffold structures described above give enough leeway to a stent designer to vary the shapes and other dimensions of the elements of the stent to effectively reduce the thickness of the stent struts imparting necessary radial strength to the stent structure and get desired fatigue resistance. As described above, it is a well-accepted fact that reduced thickness of the stent reduces injury to the walls of the body lumen.

Flexibility of the stent is decided by the thickness and number of cross linking elements across the circumference of the stent as well as their locations. If the number of these connectors is reduced, some of the sinusoidal sections become free to give more flexibility to the stent. However, this will reduce the mechanical strength of the stent.

Thus it is extremely important to strike a balance between the flexibility and the strength to optimize overall properties of the stent. The designs of stents described in specific embodiments of this invention are based on the principles described above and are generally for coronary vasculature. However, the configurations described in this invention can be varied to get different shapes of the stent such that it is possible to make stents for other applications like cerebral vasculature, renal vasculature, peripheral vasculature etc. by striking balance between strength and flexibility depending on the function. In this way, the stent structure configuration described in this invention gives enough flexibility to a stent designer to tailor the stent for any application.

Using the above general principles and specific scaffold structure design, it was possible to make bioabsorbable stents with strut thickness of approximately 130 µm or less, preferably between 100 µm and 110 µm. Thus the invention further encompasses balloon expandable stent made from bioabsorbable polymer with thin struts (strut thickness 130 µm or less, preferably 100-110 µm) with high fatigue and radial strength.

Typical stent scaffold structures are described below and shown in FIG. 4 to FIG. 7. These structures are described as typical examples and one with skill in this art will appreciate that the low strut thickness of 130 µm or less can be obtained by other designs with similar features using the principles described above.

The scaffold structure may consist of curvilinear sinusoidal shaped rows of struts. These rows are interconnected with cross linking struts to form the overall stent structure. The shape of the rows and the way the rows are interconnected can be altered to get desired mechanical strength and other essential properties of the stent like flexibility (pushability and trackability), lumen to stent surface area ratio, desired side branch access, desired crimping profile etc.

Scaffold structures designed based on above general principles are depicted in FIGS. 4, 4A, 4B, 4C, 5, 6 and 7. These structures with adequate radial and fatigue strengths can be made with strut thickness lower than 130 µm using polymer and the process of instant invention.

Figure 4:
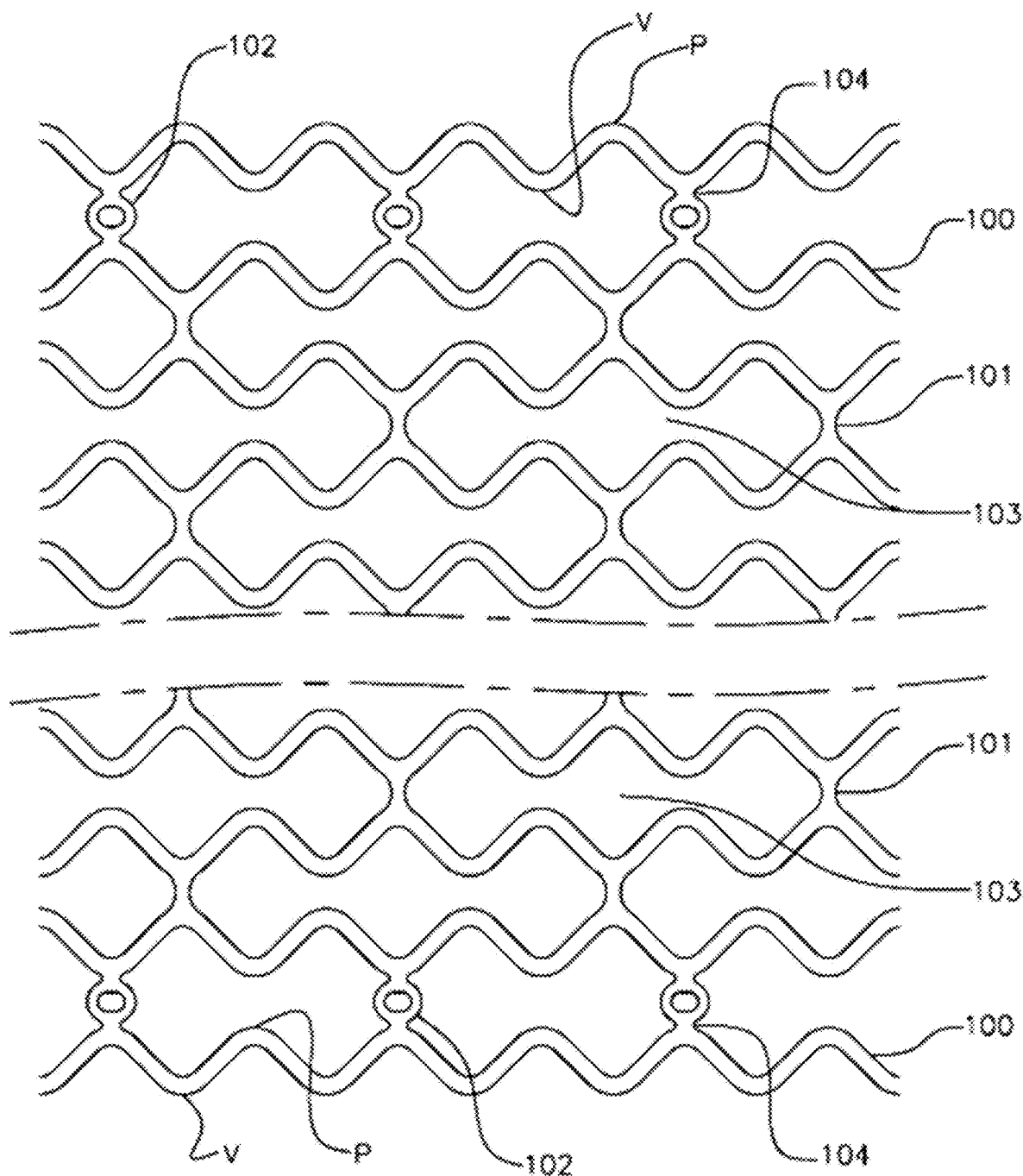
FIG. 4 depicts the scaffold structures of the stent.

FIG. 4 shows an embodiment of a stent in flattened configuration in vertical position with a preferred scaffold structure which consists of rows of curved struts 100 with sinusoidal wave like shape with peaks P and valleys V which form rings. The terms "peak" and "valley" are relative and depends on positioning of the scaffold structure. With reference to FIG. 4, peak is the portion which rises vertically up and valley is the portion which shows a dip. The rows of struts are aligned in such a way that the peaks of one row/ring face the valleys of the subsequent row/ring and vice versa. The rows/rings of wavy sinusoidally shaped struts 100 are interconnected by cross linking struts 101 to form the stent. The cross linking struts 101 connect peak of the lower row with the valley of the upper row. The placement of cross linking struts 101 is after leaving two subsequent peaks and valleys and this forms the cell 103. These struts 101 impart mechanical strength and connectivity to the structure. The length of the cross linking struts at the ends of the stent structure (104) is kept little longer than other such elements to facilitate fixing of the radio opaque markers 102. The stent made of this design using the polymer and process of instant invention demonstrated adequate mechanical strength viz. radial strength and fatigue strength required for coronary stent with 125 µm strut thickness. This structure also demonstrated adequate trackability, pushability, sufficiently large side branch access and other such essential properties.

Figure 4A:
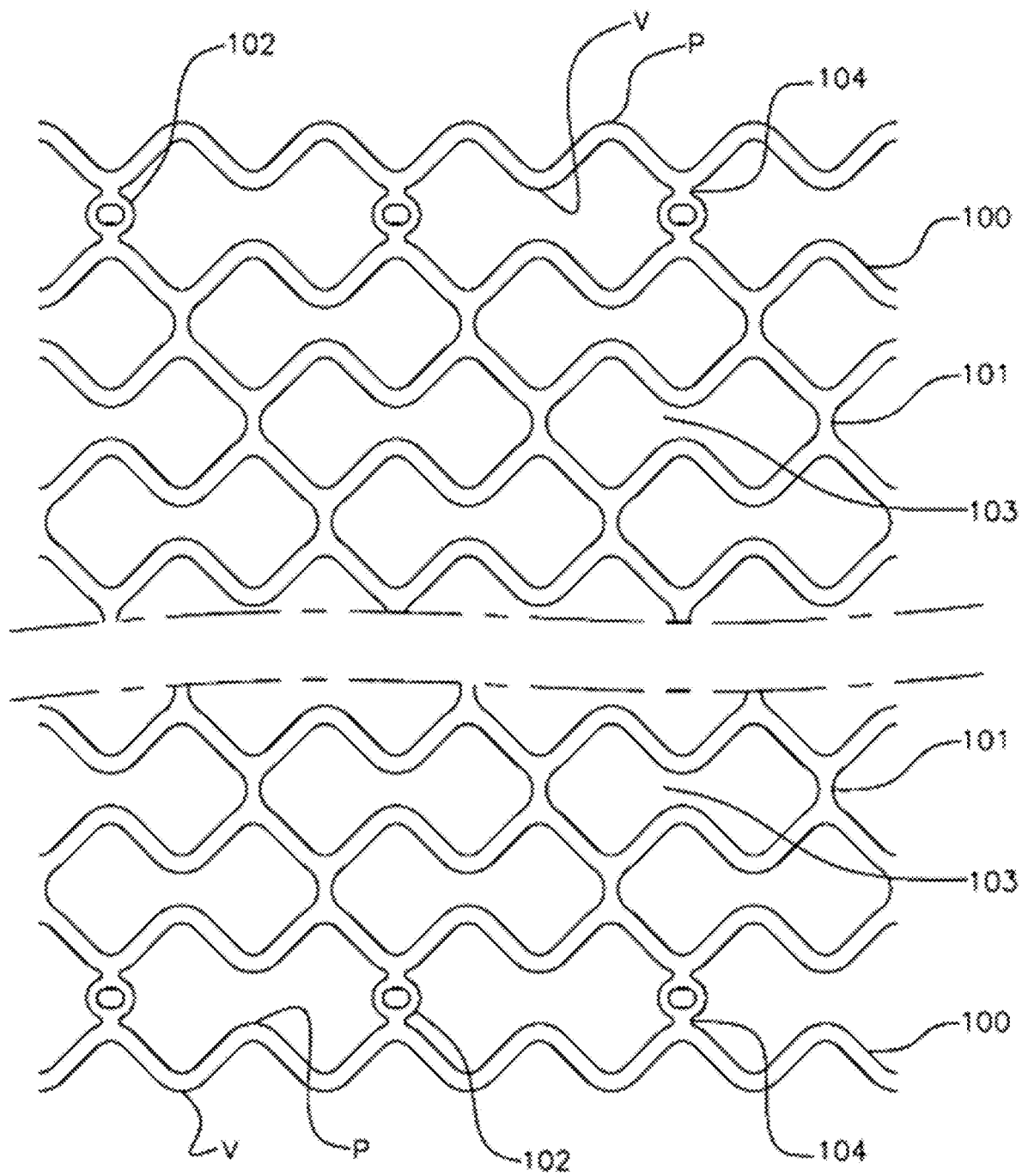
FIG. 4A depicts the scaffold structures of the stent.

The struts 101 can be placed on every alternate peak and valley as shown in FIG. 4A. This will increase the number of cross linking struts 101 in structure depicted in FIG. 4A compared to the structure depicted in FIG. 4. Increased number of these cross linking struts 101 will impart higher mechanical strength to the scaffold compared to structure depicted in FIG. 4. Thus, the structure of FIG. 4A is stronger than that of FIG. 4. Hence, same mechanical strength can be achieved in structure shown in FIG. 4A with thinner struts (<125 µm thick) compared to the structure shown in FIG. 4.

Figure 4B:
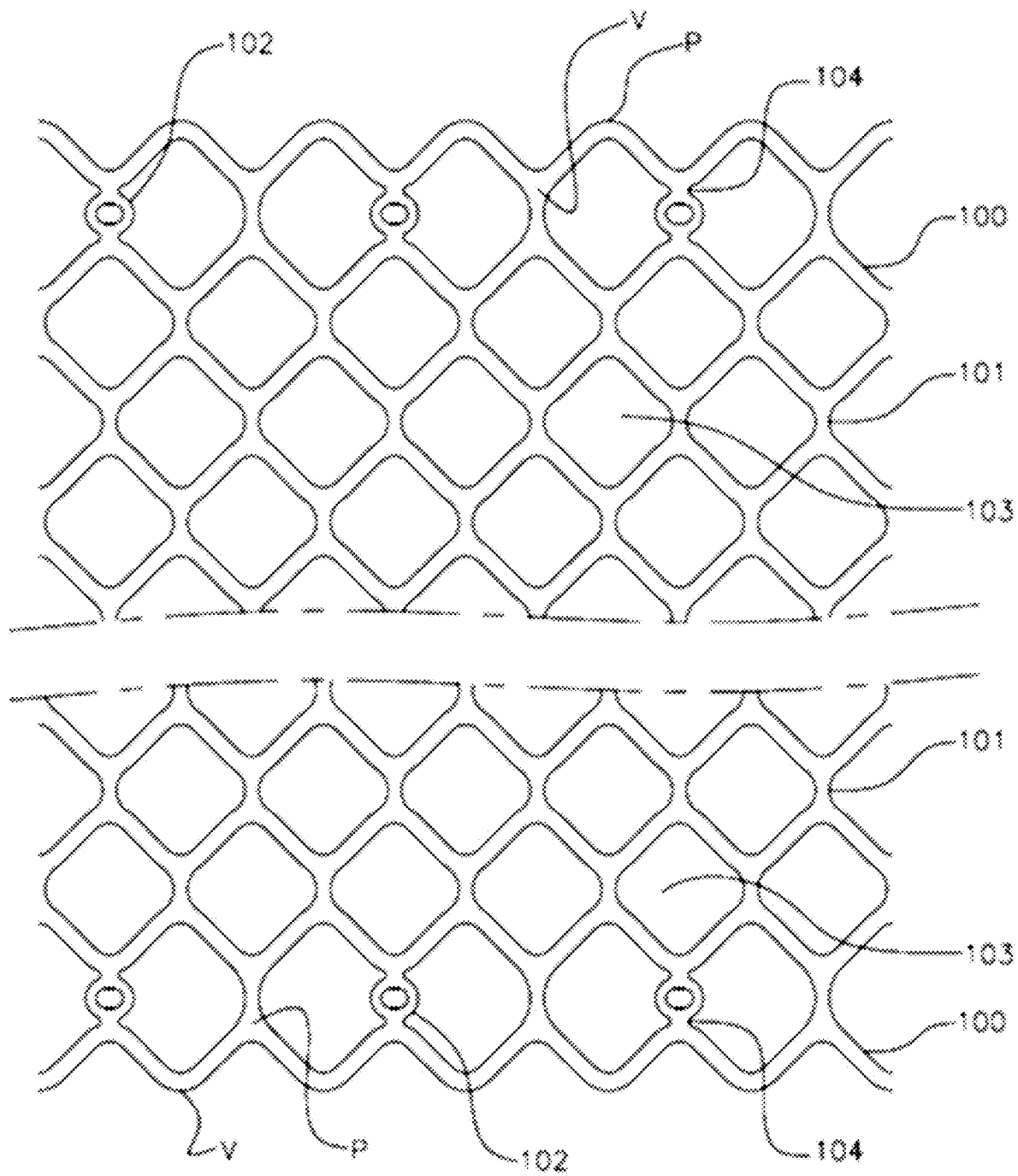
FIG. 4B depicts the scaffold structures of the stent.

In the limit, the cross linking elements can be provided at every peak and valley as shown in FIG. 4B. The strength of the stent will be maximum in this case but this design will compromise other properties like ease of crimping, flexibility, side branch access etc. Thus, one has to strike balance between strength and other properties.

Figure 4C:
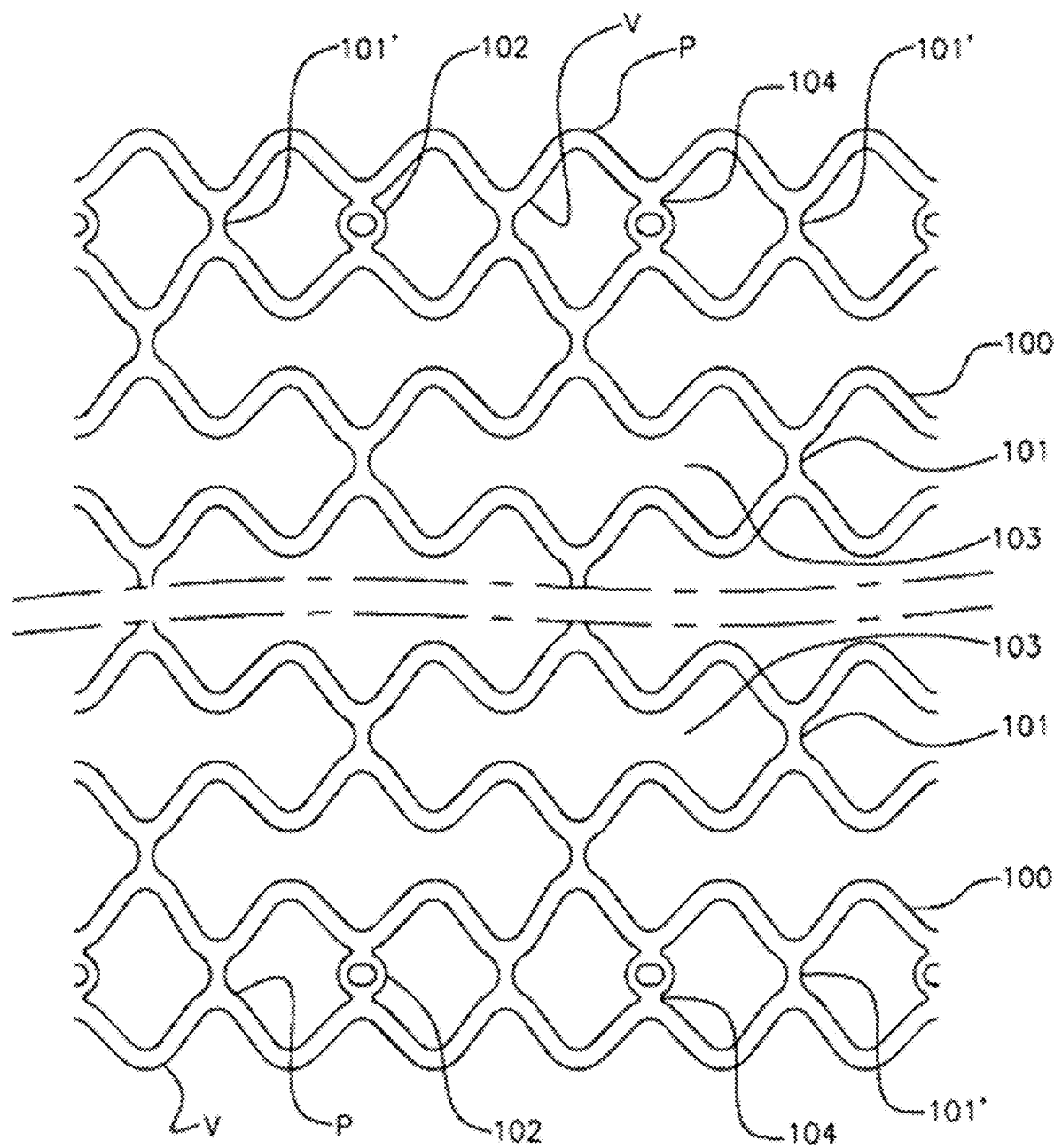
FIG. 4C depicts the scaffold structures of the stent.

A variation of the scaffold design depicted in FIG. 4 is shown in FIG. 4C. The design shown in 4C is same as that in FIG. 4 except the cells at both the ends of the stent structure are made short by connection with cross linking elements 101' at each peak and valley. Thus, the cells at the ends become mechanically stronger than the other cells. When this structure is expanded, closed cells at the ends offer more resistance to expansion compared to cells in the central portion of the stent. Hence, the stent will tend to expand from the central portion earlier than the end portions. This will result in the central portion contacting the arterial wall before the end portions. This eliminates classical "dog-boning effect" where the end portions expand before the central portion causing edge injury to the artery during implantation. The stent made of this design using the polymer and process of instant invention demonstrated adequate mechanical strength viz. radial strength and fatigue strength required for coronary stent with 105 µm strut thickness.

Figure 5:
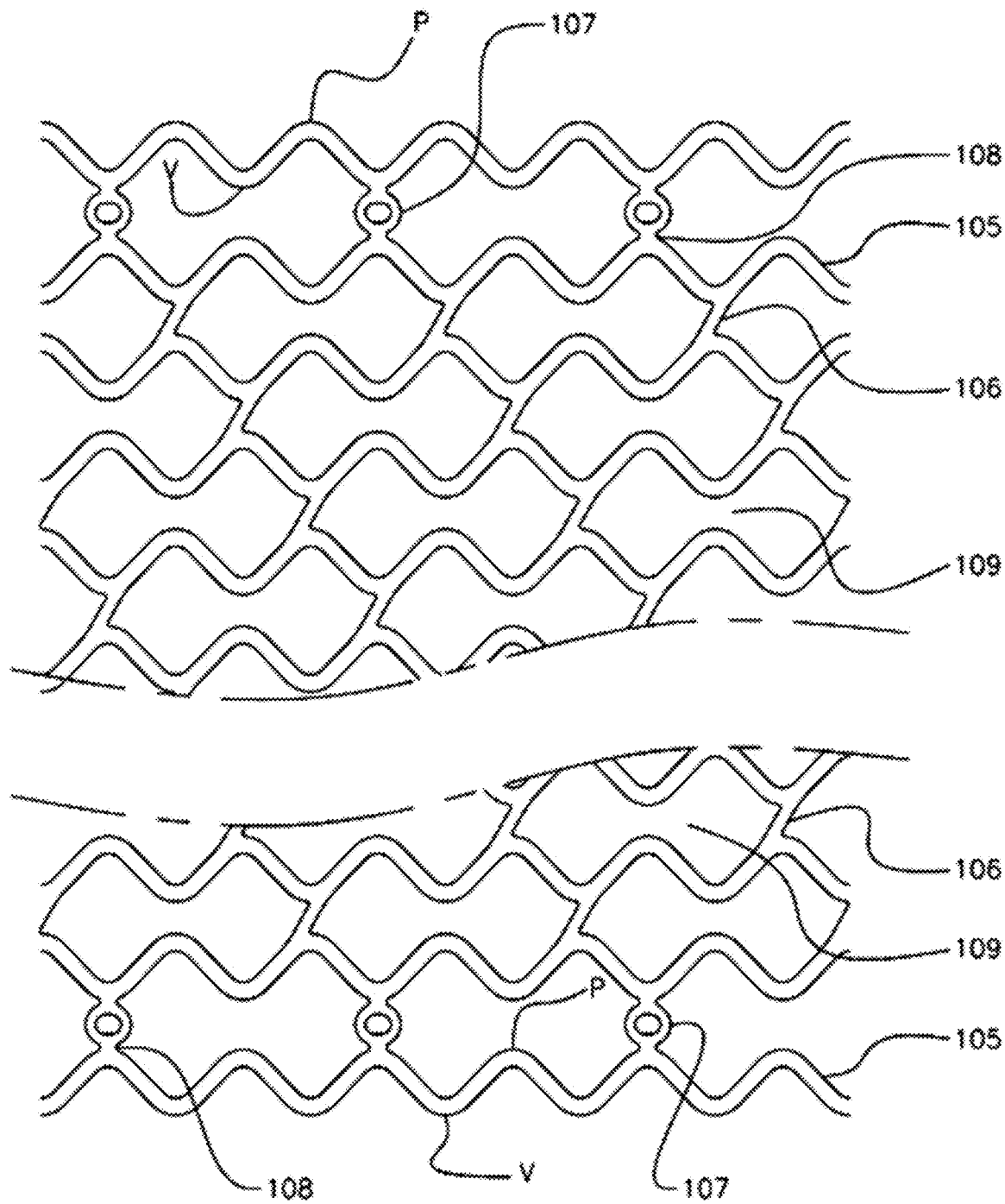
FIG. 5 depicts the scaffold structures of the stent.

A similar scaffold structure with different geometry and shape is shown in FIG. 5. This structure also contains rows of sinusoidal struts 105 with different curvature than the struts depicted in FIG. 4. The interconnecting struts 106 are not straight but are slanted. The cross linking struts 108 at the ends are kept straight and radio opaque markers 107 are located on these struts. The shape of the cell 109 is little different than the structure shown in FIG. 4. This structure will have somewhat different mechanical properties than the structure depicted in FIG. 4.

Figure 6:
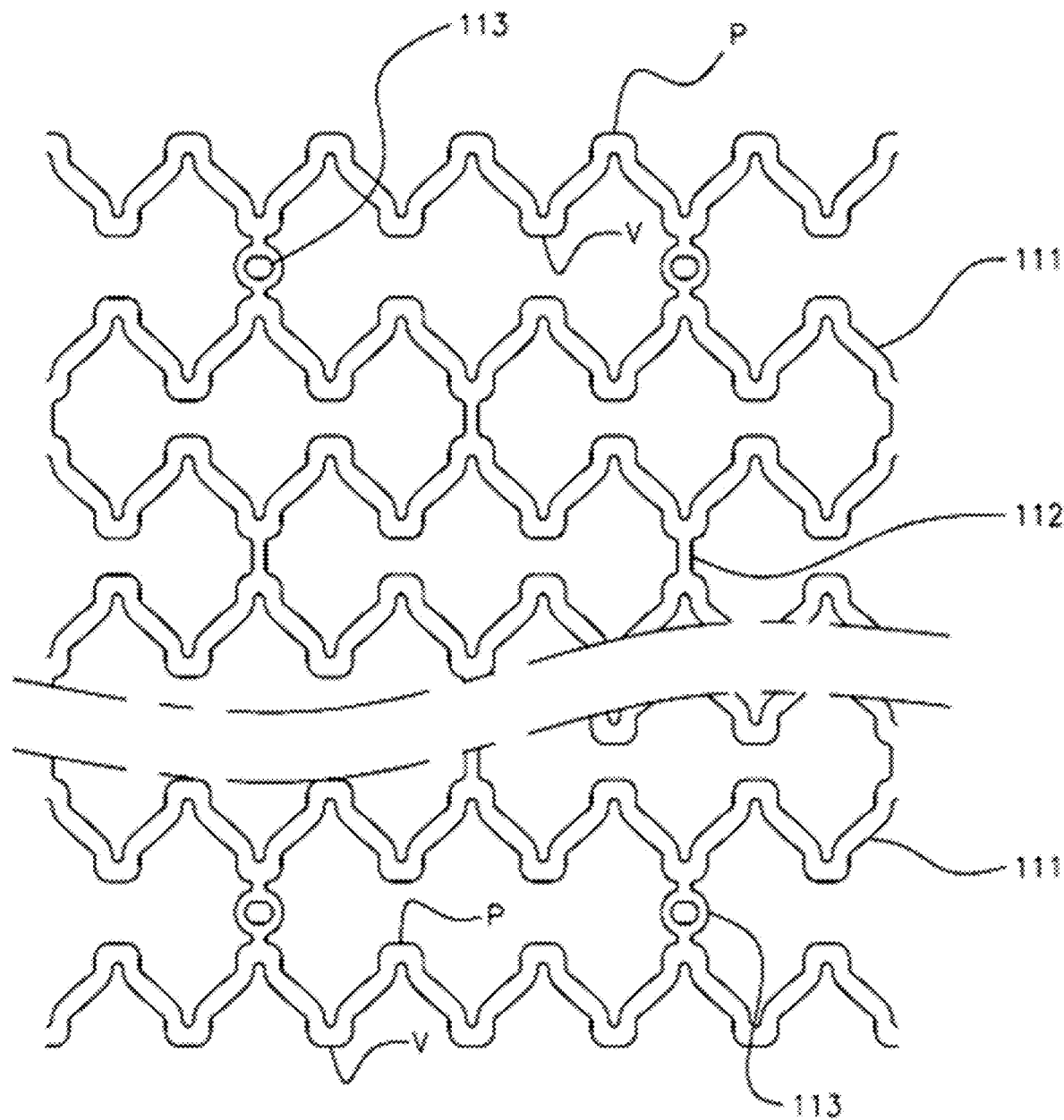
FIG. 6 depicts the scaffold structures of the stent.

A still different scaffold structure is depicted in FIG. 6. The rows 111 are wavy but not sinusoidal in shape. They have a specific shape of different design. The cross linking elements 112 are straight. The radio opaque markers 113 are fixed on the cross linking elements at the ends of the stent.

Figure 7:
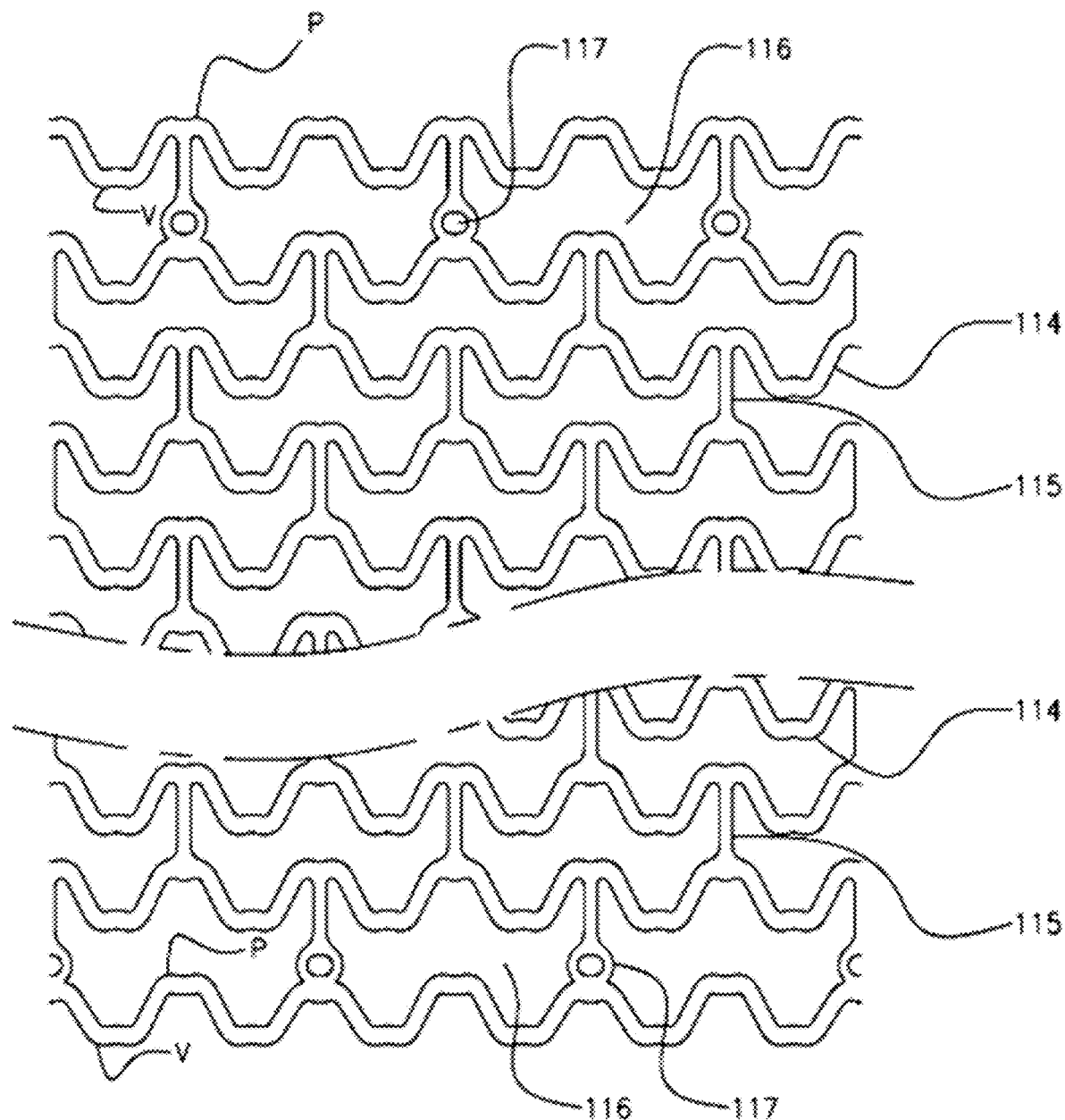
FIG. 7 depicts the scaffold structures of the stent.

A yet different scaffold structure is depicted in FIG. 7. The rows 114 are again not exactly sinusoidal in shape but they have a design different than design shown in FIG. 4 and FIG. 6. In this design, the rows of struts are aligned in such a way that the peaks of one row/ring face the peaks of the subsequent row/ring and valleys of one row/ring face the valleys of the subsequent row/ring. The rows/rings of struts 114 are interconnected by cross linking struts 115 to form the stent. The cross linking struts 115 connect peaks of consecutive rows. The placement of cross linking struts 115 is at every alternate peak and this forms the cell 116. The cross linking elements 115 are straight but longer than those in FIG. 6.

The radio opaque markers 117 are fixed on the cross linking elements at the ends of the stent.

Each of the stent designs described above follow general patterns described earlier but has different properties and strengths. Using the principles described above, one skilled in this art can generate a number of alternate designs with desired characteristics. The surface of the laser cut stent is cleaned using any solvent (e.g. iso propyl alcohol (IPA)) to remove surface defects.

Figure 8:
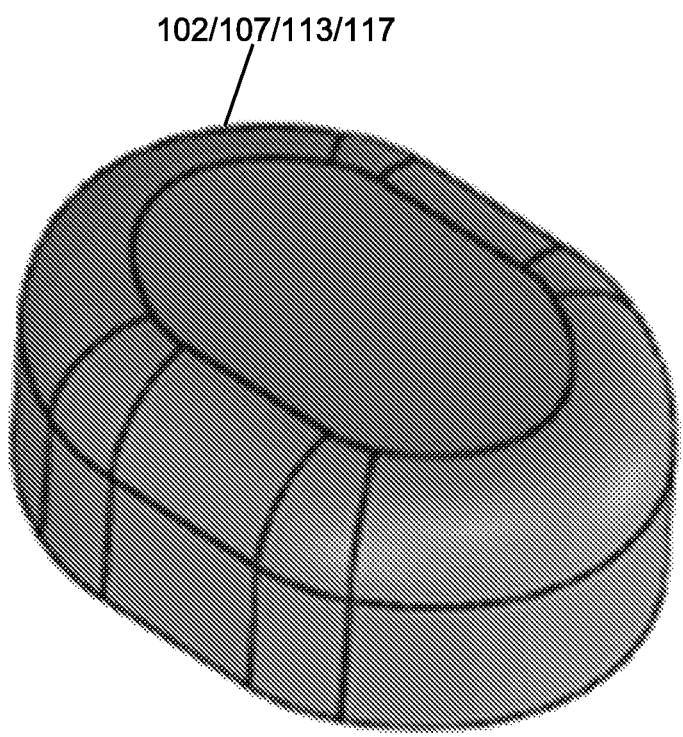
FIG. 8 depicts the shape of the radio opaque marker.

The stent should exhibit enough radio opacity for ease of implantation procedure. A polymer stent does not have adequate radio opacity to become visible in X-ray imaging. The visibility in X-ray imaging is achieved by providing radio opaque markers on the stent. The radio opaque markers help to locate the position of stent during and after the deployment with the help of X-ray imaging. In an embodiment, during the operation of laser cutting the stent pattern on the tube, holes or depots are cut in the cross linking elements located on proximal and distal ends of the stent structure where radio opaque markers are fixed. The radio opaque markers may be deposited in these holes or depots by any method (e.g. using tweezer with or without a vacuum pump which can generate vacuum of 10 to 15 inch of mercury). Radio opaque markers are made from radio opaque metals which should be biocompatible and should not interfere with the treatment site. Such metals include platinum, gold, tantalum etc. In a preferred embodiment, six platinum markers are fixed on the stent, three at each end of the stent equi-spaced circumferentially at 120° to each other. The shape of these markers is tri-axial ellipse as shown in FIG. 8. This shape is clearly visible in the X-ray imaging. This arrangement gives a clear idea of the stent position as well as patency of the stent at the ends in two standard orthogonal views without help of OCT or IVUS.

The process of placing the markers in the hole or the depot is simplified. The marker may be pressed against the hole or depot by a flat tool under optical microscope or under magnifying glass until the marker gets firmly fixed at the center of the hole or in the depot. A biocompatible adhesive may be used for better securement of a marker in the hole or the depot. The biocompatible adhesive is selected from but not limited to the compounds like polyester, polyamides, PEG, proteins, cellulose, starch and their mixtures. Suitable solvent is used for making adhesive glue. The solvent should be volatile enough to get evaporated to avoid presence of residual solvent on the stent. This solvent is selected from but not limited to the compounds like chloroform, ethanol, water, acetone or their mixtures.

In yet another embodiment, the annealing of the laser cut stent with radio opaque markers is done at temperature approximately between 90° C. and 120° C. preferably between 100° C. and 110° C. for a period of time (e.g. varying from 30 min to 16 hours, preferably from 2 hours to 8 hours and more preferably from 3 hours to 4 hours). In an embodiment, vacuum of up to 650 to 700 mm Hg (absolute pressure of 60-110 mm Hg) is applied to remove the monomers. The stent is then cooled to ambient temperature in few seconds (20 sec to 10 minutes preferably between 30 sec to 2 minutes). The stent at this stage achieves adequate mechanical strength viz. radial strength and fatigue strength. The crystallinity at this stage is between 40% and 50%. The surface of the stent is then cleaned using solvent like iso propyl alcohol (IPA), chloroform, perchloro ethylene (as such or diluted with a suitable solvent) or mixture thereof. Cleaning operation removes surface defects and makes the surface smooth. The process involves dipping the annealed stent scaffolds mounted on mandrels in the solvent mixture to clean the scaffold. Cleaning is achieved by rotating the stent in the solvent mixture for up to maximum 10 minutes at ambient temperature. The cleaned stent is dried under vacuum to remove residual solvent on the surface. The process is controlled such that desired strut thickness is achieved in this operation.

In a further embodiment, the stent is coated with formulation of therapeutic agent by spray coating method. The therapeutic agent may be antiproliferative drug/s formulated with a carrier that may allow release of the therapeutic agent in controlled manner. The therapeutic agent and the carrier may be dissolved in a suitable solvent to facilitate spray coating process. The solvent may then be removed by evaporation under vacuum. In one embodiment, a formulation consisting of Sirolimus drug and PDLLA polymer as carrier in 50:50 w/w proportions is dissolved in a suitable solvent and the solution is used for coating. The solvent is selected from compounds like methylene chloride, chloroform, acetone, methanol and mixtures thereof. The uniform and smooth coating is achieved by spraying the solution on the stent from a spray coating machine. The parameters for spray coating process need to be accurately controlled. These parameters include distance between stent and spray gun tip, collate rotation, solution flow rate and inert gas pressure used for spraying.

In a preferred embodiment, the parameters are as below.
The distance between spray gun tip and stent may be 3 cm to 10 cm, more specifically 4 cm to 6 cm.
The collate rotation speed may be between 10 and 20 rpm.
Spray gun oscillation may be between 30 and 60 per minute and more closely between 35 and 55 per minute.
The inert gas is nitrogen at 1.5 to 2.5 kg/cm$^2$ pressure.
Flow rate of the solution is kept between 0.10 and 0.40 ml/min, more specifically between 0.15 and 0.30 ml/min.
After coating process, the stent is kept under vacuum to remove the solvent.

The stent (with or without coating) is then crimped on the balloon of the catheter. Crimping operation is very critical. It should not affect the stent surface and cause no mechanical damage to the coating or to the stent. Crimping parameters include diameter of stent after crimping, pressure of crimping, dwell time and temperature. Crimping operation can alter properties of the polymer and hence the properties of the stent. The stent length and balloon size affect the crimping operation. For effective crimping, the crimping parameters change with stent length and balloon size. In a preferred embodiment, crimping is done in 6 to 8 stages with dwell time between 200 to 310 seconds. The crimping temperature is kept between 25° C. and 40° C. Finally, the stent prepared according to the invention is sterilized (e.g. using e-beam sterilization process). E-beam method is commonly used for the sterilization of medical devices because e-beam radiation can provide much higher dosing rate compared to gamma rays or X-rays which reduces the exposure time which in turn reduces potential degradation of the polymer. Another advantage is that the sterilization process leaves no residue. The sterilization is conducted at ambient or lower than ambient temperature to avoid temperature related degradation of polymer.

It is known that e-beam radiation causes degradation of polymer and thus has a significant effect on the average molecular weight $M_w$ and average molecular mass $M_n$ of the bioabsorbable polymers and hence its mechanical properties. We studied the effect of e-beam radiation over a wide range of doses varying from as low as 5 kGy to as high as 50 kGy. The objective was to study the effect of e-beam dose on $M_w$ and $M_n$. The reduction in $M_w$ varied from as low as 23% for e-beam dose of 5 kGy to as high as 58% for dose of 50 kGy. Reduction in $M_n$ varied from as low as 32% for e-beam dose of 5 kGy to 67% for dose of 50 kGy.

It is hence very essential to reduce the e-beam dose to minimize the polymer degradation.

The effect of e-beam dose on the degradation of polymer can be reduced to some extent by adding a stabilizer in the polymer matrix. This stabilizer should be biocompatible and should not create any adverse clinical effect.

Normal dose of e-beam for effective sterilization is more than 20 kGy. The instant invention reduces the degradation by reducing the dose of e-beam considerably without compromising effective sterilization and without use of a stabilizer. The sterilization process of instant invention is done in two parts as described hereafter.

The stent system consists of components like stent, and delivery catheter. The e-beam dose affects the polymer stent and not the other components. In an embodiment, all components of the stent system other than the stent are sterilized separately using either Ethylene Oxide (ETO) or e-beam. The polymer stent is then mounted on the sterilized catheter in clean environment by crimping process. The assembly along with the crimped stent is then subjected to e-beam sterilization at a temperature approximately between 15° C. and 25° C.

Using this process, the effective sterilization was achieved with e-beam dose lower than about 15 kGy; preferably between 5 kGy and 12 kGy, which is much lower than the normal effective dose of more than 20 kGy. The change in average molecular weight $M_w$ of the polymer after sterilization varied from about 23% to 40% depending on the dose level. This method resulted in acceptable bio burden of less than 3 cfu and Sterility Assurance Level (SAL) of "six log reduction" (10-6). The sterilization did not have any significant effect on the optical rotation or crystallinity.

Following cases exemplify the process of sterilization and its effect on molecular weights of the polymer. These cases are described for purpose of explanation and they do not limit the invention in any way.

Case-1:
The stent with $M_w$ of 378,240 and $M_n$ of 211740, crystallinity of around 48% and radial strength around 31 N was subjected to the above sterilization process. The catheter and other components were sterilized using ETO. The unsterilized stent was crimped on the balloon of the sterilized catheter in clean environment and the assembly was packed in appropriate manner for e-beam sterilization with e-beam dose of 10 kGy at 15° C. The dose resulted in effective sterilization. $M_w$ and $M_n$ after sterilization were 275940 and 131310 respectively, crystallinity 47% and radial strength of 27 N. The reductions in $M_w$ and $M_n$ were 27% and 38% respectively. PDI changed from 1.79 to 2.1. The specific rotation was −158°.

Case-2:
The stent with $M_w$ of 360980 and $M_n$ of 200550, crystallinity of 51% and radial strength around 32 N was subjected to the above sterilization process. The catheter and other components were sterilized using ETO. The unsterilized stent was crimped on the balloon of the sterilized catheter in clean environment and the assembly was packed in appropriate manner for e-beam sterilization. Effective sterilization was achieved with e-beam dose of 6 kGy at 15° C. $M_w$ and $M_n$ after sterilization were 268930 and 132760 respectively, crystallinity 49% and radial strength of 28 N. The reductions in $M_w$ and $M_n$ were 25.5% and 33.8% respectively. PDI changed from 1.8 to 2.03. The specific rotation was −161°.

Case-3:
The stent with $M_w$ of 345460 and $M_n$ 189900 was subjected to e-beam sterilization process. The e-beam dose was 25 kGy at 15° C. $M_w$ and $M_n$ after sterilization were 206250 and 91152 respectively. The reductions in $M_w$ and $M_n$ were 40.3% and 52% respectively. PDI changed from 1.82 to 2.26. The specific rotation was −158°.

Case-4:
The stent with $M_w$ of 352670 and $M_n$ 192750 was subjected to e-beam sterilization process. The e-beam dose was 45 kGy at 15° C. $M_w$ and $M_n$ after sterilization were 165750 and 71320 respectively. The reductions in $M_w$ and $M_n$ were 53% and 63% respectively. PDI changed from 1.83 to 2.32. The specific rotation was −154°.

EXAMPLES

The following examples are only for illustrating and help understanding the invention. They do not limit the invention in any manner.

Example-1

The starting material for making the stent was extruded PLLA tube with $M_w$ of 591280, $M_n$ of 354890, PDI 1.67, specific rotation of −158° and glass transition temperature 60° C. and crystallinity 9%. The tube was deformed at 74° C. by applying axial force till desired stretch was achieved to get axial expansion ratio of 1.6. The conditions were maintained for 15-20 sec and then the axial force was removed. The radial expansion was then carried out by pressurizing the tube with nitrogen in 3 stages at 74° C. to achieve radial deformation ratio of 4.
Stage-1: 270 psi.
Stage-2: 390 psi.
Stage-3: 520 psi.
At each stage, the conditions were maintained for 15-20 sec.

While maintaining the pressure, the tube was heated to 110° C. over about 1 min and this temperature was maintained for 1 min. The tube was then cooled to 20° C. over about 30 sec. The pressure was then released and the tube was removed from the mold.

The $M_w$, $M_n$ and PDI of the deformed tube at the end were 518350 (reduction of 12.3%), 324760 (reduction of 8.5%) and 1.596 respectively. It is evident that the molecular weight distribution was narrower after processing which is advantageous. (Single stage processing of the same tube at 150 psi pressure to achieve same radial deformation ratio, i.e. 4, resulted into 16.2% reduction in $M_w$, 18.0% reduction in $M_n$, and PDI 1.7).

The deformed tube was cleaned with iso propyl alcohol and then cut on laser machine using laser beam of 1400 nm wave length with pattern of FIG. 4C to form the stent. The laser cut stent was annealed at 105° C. for 3.5 hours under vacuum of 700 mm Hg. The stent was then cooled to ambient temperature in 1 minute. The $M_w$, $M_n$ and PDI of the processed stent were 447620 (reduction of 13.6%), 248160 (reduction of 23.6%) and 1.804 respectively. The crystallinity at this stage was 48%. The stent was then cleaned by rotation for 10 min in perchloro ethylene at ambient temperature. At the end of this operation, the strut thickness of 105 μm was achieved. Three platinum radio opaque markers of the shape depicted in FIG. 8 were fixed at each end of the stent without use of adhesive in the holes formed during laser cutting operation.

The stent was then crimped at 35° C. under clean environment on pre-sterilized PTCA catheter in 8 stages and total dwell time of 250-270 sec.

The stent system was effectively sterilized using e-beam dose of 6 kGy at 18° C. $M_w$, $M_n$ and PDI of sterilized stent were 332130 (reduction of 25.8%), 163290 (reduction of 34.2%) and 2.03 respectively.

The stent demonstrated radial strength of 20-25 N depending on stent dimensions and adequate fatigue strength.

Example-2

The starting material for making the stent was extruded PLLA tube with $M_w$ of 605440, $M_n$ of 366920, PDI 1.65, glass transition temperature 62° C., crystallinity 11.5%, and optical rotation of −159 0.2°.

The tube was deformed at 75° C. by applying axial force till desired stretch was achieved to get axial expansion ratio of 1.5. The conditions were maintained for 15-20 sec and then the axial force was removed. The radial expansion was then carried out by pressurizing the tube with nitrogen in 3 stages at 75° C. to achieve radial deformation ratio of 3.9.
Stage-1: 280 psi.
Stage-2: 400 psi.
Stage-3: 510 psi.
At each stage, the conditions were maintained for 15-20 sec.

While maintaining the pressure, the tube was heated to 100° C. over 1 min and this temperature was maintained for 1 min. The tube was cooled to 20° C. over 30 sec and pressure was released. The tube was then removed from the mold.

The $M_w$, $M_n$ and PDI of the deformed tube at the end were 526460 (reduction of 13.05%), 326980 (reduction of 10.9%) and 1.61 respectively. It is evident that the molecular weight distribution was narrower after processing which is advantageous.

The deformed tube was cleaned with iso propyl alcohol and then cut on laser machine using laser beam of 1500 nm wave length with pattern of FIG. 4C to form the stent. The laser cut stent was annealed at temperature at 105° C. for 3.5 hours under vacuum of 700 mm Hg. The stent was then cooled to ambient temperature in 1 minute. The $M_w$, $M_n$ and PDI of the processed stent were 450120 (reduction of 14.5%), 248460 (reduction of 24.0%) and 1.812 respectively. The crystallinity at this stage was 46%.

The stent was then cleaned by rotation for 10 min in perchloro ethylene at ambient temperature. At the end of this operation, the strut thickness was 110 μm was achieved. Three platinum radio opaque markers of the shape depicted in FIG. 8 were fixed at each end of the stent without use of adhesive in the holes formed during laser cutting operation. The stent was then crimped under clean environment on pre-sterilized PTCA catheter at 38° C. in 7 stages and total dwell time of 240-260 sec. The stent system was effectively sterilized using e-beam dose of 10 kGy at 18° C. $M_w$, $M_n$ and PDI of sterilized stent were 321830 (reduction of 28.5), 161240 (reduction of 35.1%) and 2.0 respectively.

The stent demonstrated radial strength of 20-25 N depending on stent dimensions and adequate fatigue strength.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A process for the preparation of a biodegradable stent, the process comprising:
   providing an extruded biodegradable polymer tube;
   deforming the extruded biodegradable polymer tube axially at a first predefined temperature by applying an axial force for a first predefined time interval to form an axially stretched tube;
   radially expanding the axially stretched tube at a second predefined temperature by pressurizing the tube with an inert gas in two or more successive stages, the pressure applied in each successive stage being higher than the pressure applied in a previous stage and the pressure applied being held for at least a predefined period of time in each successive stage;

cutting a specific pattern of scaffold structure on the expanded tube by laser machining to form a laser cut stent; and crimping the laser cut stent on the balloon of delivery catheter in a clean environment in multiple stages.

2. The process of claim 1 wherein the biodegradable polymer comprises PLLA (poly-L-Lactide).

3. The process of claim 1 wherein the first predefined temperature is approximately 60°-80° C.

4. The process of claim 1 wherein the first predefined time interval is 15-20 secs.

5. The process of claim 1 wherein the second predefined temperature is approximately 60°-80° C.

6. The process of claim 1 wherein the pressurizing the axially stretched tube includes pressurizing the tube in three stages with a first stage having a pressure of approximately 250-520 psi, a second stage having a pressure of approximately 375-600 psi and a third stage having a pressure of approximately 500-670 psi.

7. The process of claim 1 wherein the inert gas is nitrogen.

8. The process of claim 1 wherein the axially stretched tube has an elongation ratio between 1.05 and 1.7.

9. The process of claim 1 further comprising
heating the radially deformed tube between 100° C. and 125° C. for up to maximum 2 mins; and
cooling the radially deformed tube to 20° C. in 20-30 sec to obtain a finished deformed tube.

10. The process according to claim 1, wherein the laser cutting operation of the finished deformed tube is done at a wave length between 1300 and 1600 nm.

11. The process according to claim 1, wherein the laser cut stent is annealed before or after depositing the one or more radio opaque markers at temperature between 100° C. and 110° C. for a period varying from 3 hours to 4 hours under vacuum of up to 650 to 700 mm Hg to form an annealed stent followed by cooling the stent to ambient temperature in 25-30 sec.

12. The process according to claim 11, wherein cleaning of the annealed stent with radio opaque markers is done using a solvent by rotation in perchloro ethylene as such or diluted in a suitable solvent or in a mixture of iso propyl alcohol and chloroform to form a cleaned stent.

13. The process according to claim 12, wherein the cleaned stent is coated with a formulation of an antiproliferative drug and a carrier polymer by a spray coating method.

* * * * *